(12) United States Patent
Fontaine et al.

(10) Patent No.: US 12,741,116 B2
(45) Date of Patent: Sep. 22, 2026

(54) GAS-DRIVEN, PRESSURE-REGULATED VENTILATOR

(71) Applicant: OREGON HEALTH & SCIENCE UNIVERSITY, Portland, OR (US)

(72) Inventors: Evan Fontaine, Portland, OR (US); Whitney Menzel, Portland, OR (US); Albert Chi, Portland, OR (US)

(73) Assignee: Oregon Health & Science University, Portland, OR (US)

(*) Notice: Subject to any disclaimer, the term of this patent is extended or adjusted under 35 U.S.C. 154(b) by 947 days.

(21) Appl. No.: 18/002,449

(22) PCT Filed: Jun. 14, 2021

(86) PCT No.: PCT/US2021/037260

§ 371 (c)(1),
(2) Date: Dec. 19, 2022

(87) PCT Pub. No.: WO2021/257472

PCT Pub. Date: Dec. 23, 2021

(65) Prior Publication Data

US 2023/0226305 A1 Jul. 20, 2023

Related U.S. Application Data

(60) Provisional application No. 63/113,096, filed on Nov. 12, 2020, provisional application No. 63/041,736, filed on Jun. 19, 2020.

(51) Int. Cl.
*A61M 16/20* (2006.01)

(52) U.S. Cl.
CPC ........ *A61M 16/207* (2014.02); *A61M 16/206* (2014.02); *A61M 2205/3331* (2013.01); *A61M 2240/00* (2013.01)

(58) Field of Classification Search
CPC ........... A61M 16/20–209; A61M 16/08–0891; A61M 2205/3331; A61M 2205/3334
See application file for complete search history.

(56) References Cited

U.S. PATENT DOCUMENTS 2,996,071 A * 8/1961 Takaoka .............. A61M 16/209 251/75
3,561,466 A * 2/1971 Carden .............. A61M 16/209 128/205.24

(Continued)

OTHER PUBLICATIONS

Chi, Albert, "OHSU 3D Printed CRISIS Ventilator", Journal of Surgery and Surgical Research, May 29, 2020, 5 pages.

(Continued)

*Primary Examiner* — Valerie L Woodward
(74) *Attorney, Agent, or Firm* — Foster Garvey PC

(57) ABSTRACT

A gas-driven, pressure-regulated ventilator (10, 210) provides support for spontaneous breathing and non-breathing patients. The ventilator provides short pressure cycled and constant flow ventilatory support that allows the patient to receive consistent and reliable ventilatory breaths. The ventilator is designed to allow a clinician to adjust Peak Inspiratory Pressure (PIP) and Positive End Expiratory Pressure (PEEP) values and the duration of inhalation and exhalation flows in a breath cycle to accommodate patient-specific ventilation needs.

24 Claims, 23 Drawing Sheets

(56) References Cited

U.S. PATENT DOCUMENTS

| | | | | |
|---|---|---|---|---|
| 4,039,139 | A * | 8/1977 | Bird | A61M 16/0841 137/853 |
| 4,941,469 | A | 7/1990 | Adahan | |
| 6,067,984 | A | 5/2000 | Piper | |
| 2009/0139522 | A1 | 6/2009 | Thomson et al. | |
| 2010/0199991 | A1 | 8/2010 | Koledin | |
| 2010/0206310 | A1* | 8/2010 | Matsubara | A61M 16/209 128/205.24 |
| 2011/0088697 | A1 | 4/2011 | Devries et al. | |
| 2011/0168180 | A1* | 7/2011 | Lugtigheid | A61M 16/208 128/205.24 |
| 2011/0197892 | A1* | 8/2011 | Koledin | A61M 16/0866 128/205.24 |
| 2014/0283831 | A1* | 9/2014 | Foote | A61M 16/202 128/204.19 |

OTHER PUBLICATIONS

Ventilators available with the flip of a switch OHSU team designs low-cost ventilators using 3D-printing technology, https://news.ohsu.edu/2020/04/24/ventilators-available-with-the-flip-of-a- switch, Apr. 24, 2020, 7 pages.

* cited by examiner 94
106
100
68
98
10
84
70
12
34
34
78
80
86
88
14
124
42
138
24
122
128
136
132
120
126
130

94
106
68
98
100
10
84
70
12
34
80
78
34
86
14
88
124
42
138
24
122
128
136
132
120
126
130

GAS-DRIVEN, PRESSURE-REGULATED VENTILATOR

RELATED APPLICATIONS

This application is a National Stage of International Application No. PCT/US2021/037260, filed Jun. 14, 2021, which claims priority benefit of U.S. Provisional Patent Application No. 63/113,096, filed on Nov. 12, 2020, and U.S. Provisional Patent Application No. 63/041,736, filed on Jun. 19, 2020, titled "GAS-DRIVEN, PRESSURE-REGULATED VENTILATOR" all of which are hereby incorporated by reference in their entireties.

COPYRIGHT NOTICE

© 2021 Oregon Health & Science University. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR § 1.71(d).

TECHNICAL FIELD

This disclosure relates to a device that can be used to perform mechanical ventilation of a patient's lungs. The device is driven by a pressurized gas source and is designed to allow cyclic lung ventilation between specified Peak Inspiratory Pressure (PIP) and Positive End Expiratory Pressure (PEEP) values, as might be prescribed for patients suffering from acute respiratory distress syndrome (ARDS).

BACKGROUND INFORMATION

The worldwide pandemic of COVID-19 and attendant surge in patients requiring extended hospital stays have strained healthcare infrastructure and revealed shortages of critical supplies and equipment. As one example, a substantial number of COVID-19 patients develop ARDS and require admission to intensive care units (ICU) to receive mechanical ventilatory support. This population of patients poses a substantial challenge to the healthcare system, in part, because the nationwide stock of available ventilators to treat them is insufficient for the demand. These ventilators can be critical for patient survival, because they provide a controlled delivery of gases (oxygen and carbon dioxide) to support a patient in respiratory failure until their own immune system can mount a defense to the SARS-CoV-2 virus. For patients with COVID-19-associated ARDS, ventilatory support can entail a prolonged period of intubation, sometimes on the order of weeks or months, and can require the use of specialized lung protective strategies including higher PEEP ventilation, lower tidal volumes, and higher frequency rates. While modern ventilators used in hospital settings are able to accommodate these specialized ventilation strategies, the devices tend to be large, functionally complex, and expensive. As such, and importantly, these modern ventilators are ill-suited to triage situations that can arise during an infection surge, when ICU capacity may be exceeded and a subset of patients may need to be transported to field hospitals operating in austere environments. In these field hospitals, the space afforded to each patient may be considerably constrained and the oxygen supply available for ventilation may come from a variety of sources. Thus, there exists a need for a compact, easy-to-operate, and inexpensive device that can be deployed during ventilator shortages or in austere environments with non-standard oxygen gas supplies to meet the specialized mechanical ventilation needs described above.

SUMMARY OF THE DISCLOSURE

A gas-driven, pressure regulated ventilator device is configured to perform mechanical ventilation of a patient's lungs when used in conjunction with a pressurized gas source. The ventilator is comprised of a hollow valve body including an interior and a breathing gas pathway. The breathing gas pathway is in fluid communication with a gas inlet from a pressurized gas source to provide a supply of gas flow within the interior of the valve body. The valve body includes, at the breathing gas pathway, a gas inlet opening to allow gas flow into the interior and a gas outlet opening to allow the exhaust of gas from the interior. An adjustable PIP valve mechanism associated with the valve body includes a gas-pressure responsive displacement member that, in response to gas pressure within the breathing gas pathway, changes position between an open and a closed configuration to allow or impede, respectively, gas flow into the interior of the valve body. A spring support member operatively connected to the valve body and to a spring-actuated member is configured to apply an adjustable amount of force to the gas-pressure responsive displacement member in a direction opposite that of the force applied to gas-pressure responsive displacement member by gas pressure within the breathing gas pathway. An adjustable gas flow rate valve mechanism is operatively associated with valve body and configured to allow a controllable amount of gas flow out of the valve body through the gas outlet opening when the gas-pressure responsive displacement member is in the open position. The adjustable gas flow rate valve mechanism includes a flow control dial that, in cooperation with an arcuate slot, allows an increasing amount of gas flow through the gas outlet opening in response to rotation of the flow control dial to cause more complete alignment of the arcuate slot with the gas outlet opening.

Embodiments include a ventilator having a valve body of generally cylindrical shape comprising a base portion and a detachable pressure adjustment portion. The base portion includes a first locking feature configured to mate with a second locking feature included on pressure adjustment portion. These locking features releasably secure together the base portion and the pressure adjustment portion when the ventilator is in use and facilitate its disassembly for cleaning and sterilization of interior and exterior surfaces of components between uses.

Embodiments are configured to allow a clinician or operator to adjust the PIP and PEEP values, and to adjust the duration of inhalation and exhalation over a breath cycle to accommodate patient-specific ventilation needs. Embodiments allow for ventilation of both neonatal and adult patients over a range of PIP and PEEP values with control of inhalation:exhalation time ratios. Embodiments may also incorporate a feature to allow the operator to perform complete manual control of patient ventilation if desired.

Additional aspects and advantages will be apparent from the following detailed description of preferred embodiments, which proceeds with reference to the accompanying drawings.

DETAILED DESCRIPTION OF PREFERRED EMBODIMENTS

Figure 1:
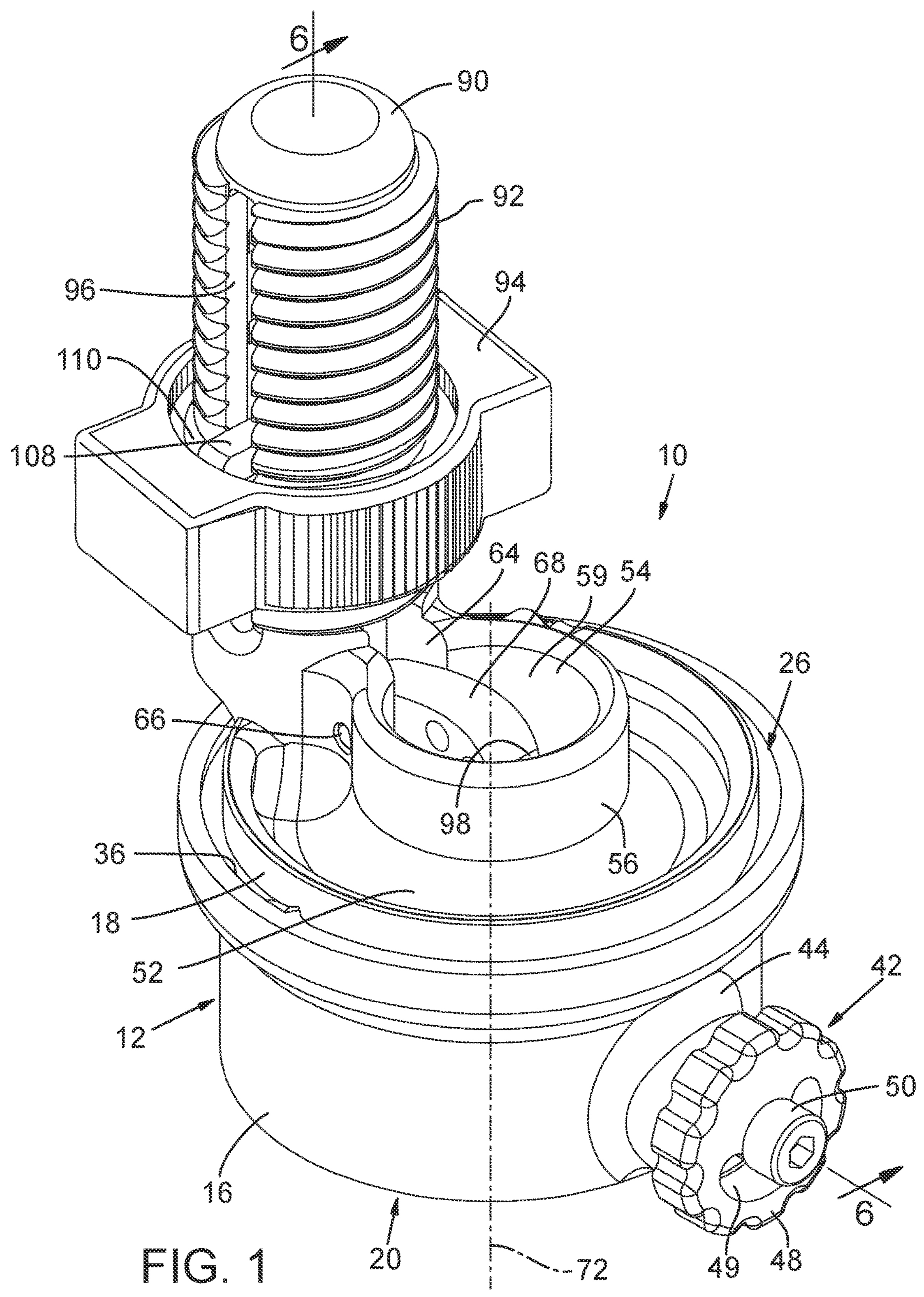
FIG. 1 is an isometric view of a first embodiment of the disclosed gas-driven, pressure-regulated ventilator.
Figures 2, 3:
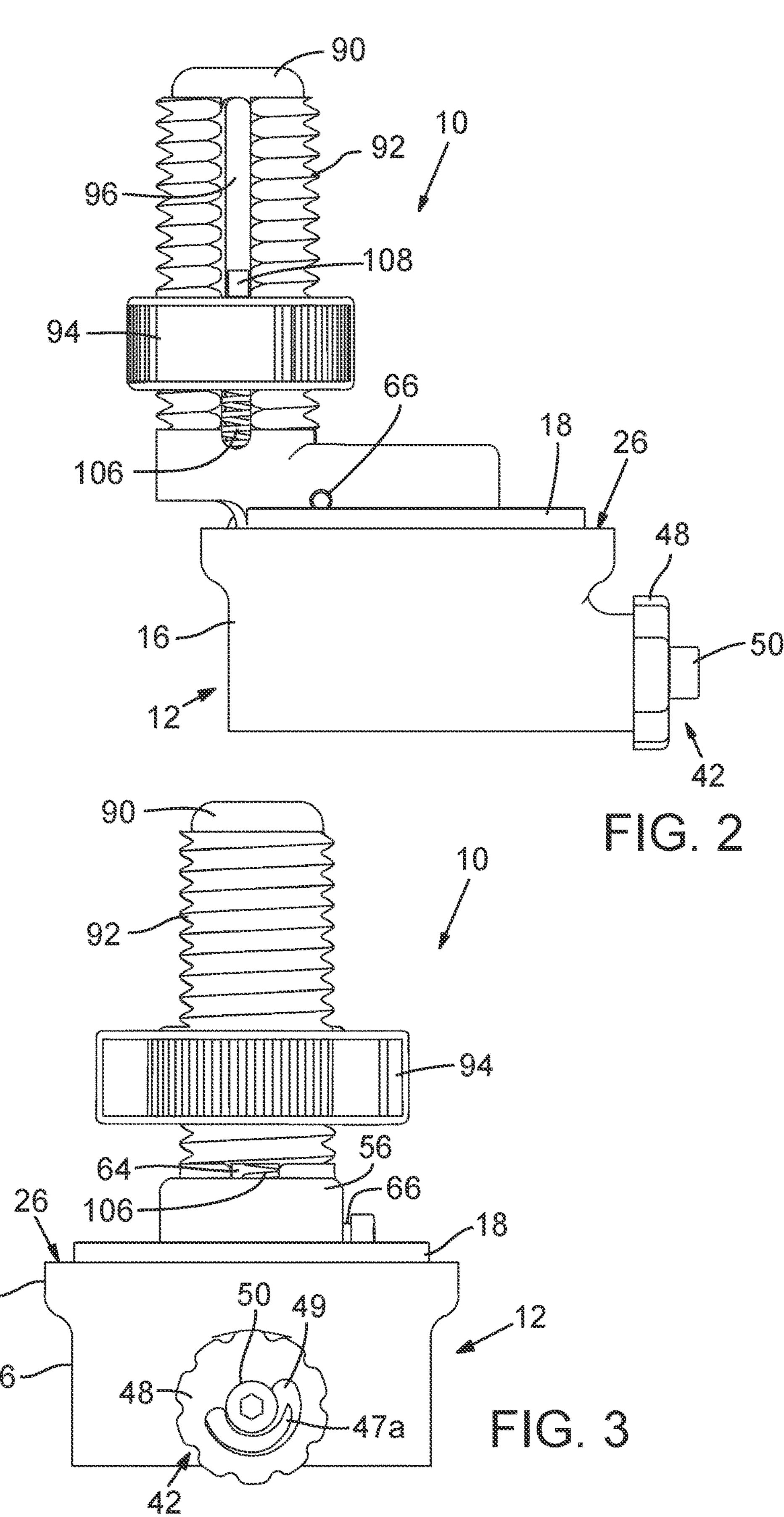
FIG. 2 is a right-side elevation view of the ventilator of FIG. 1.
FIG. 3 is a front-side elevation view of the ventilator of FIG. 1.
Figure 4:
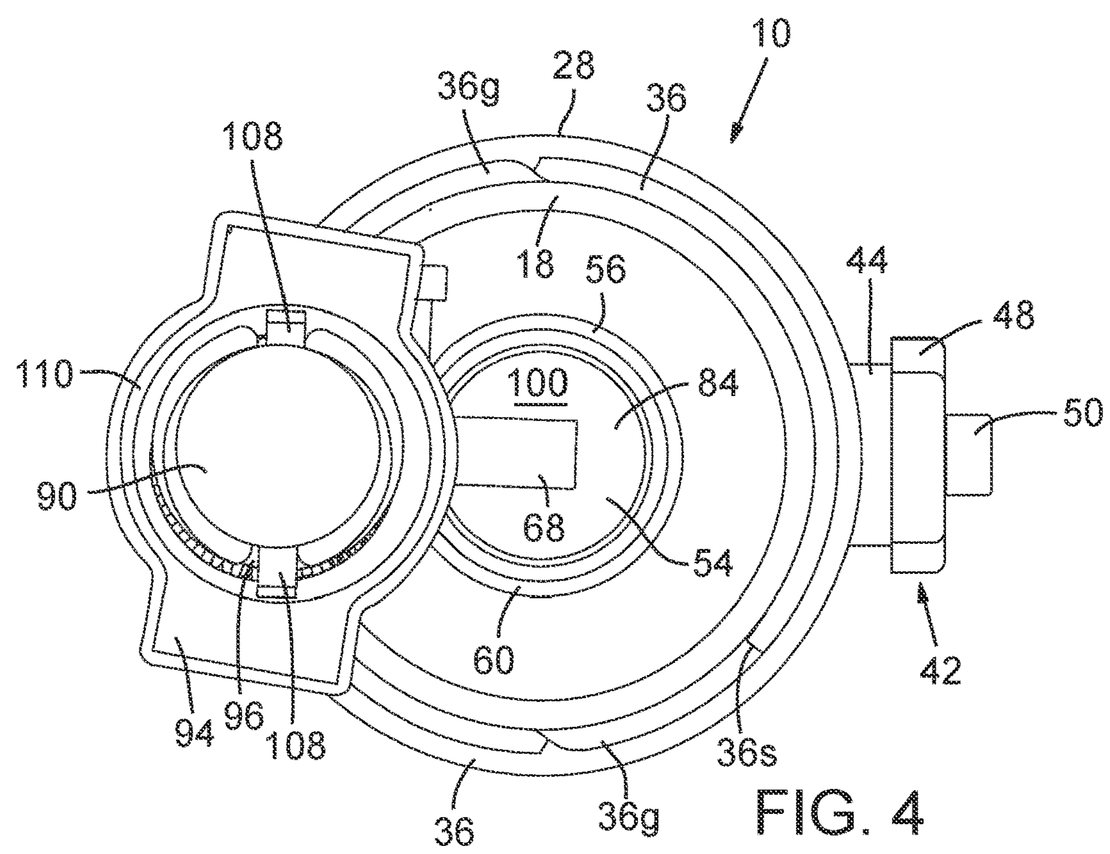
FIG. 4 is a top plan view of the ventilator of FIG. 1.
Figure 5:
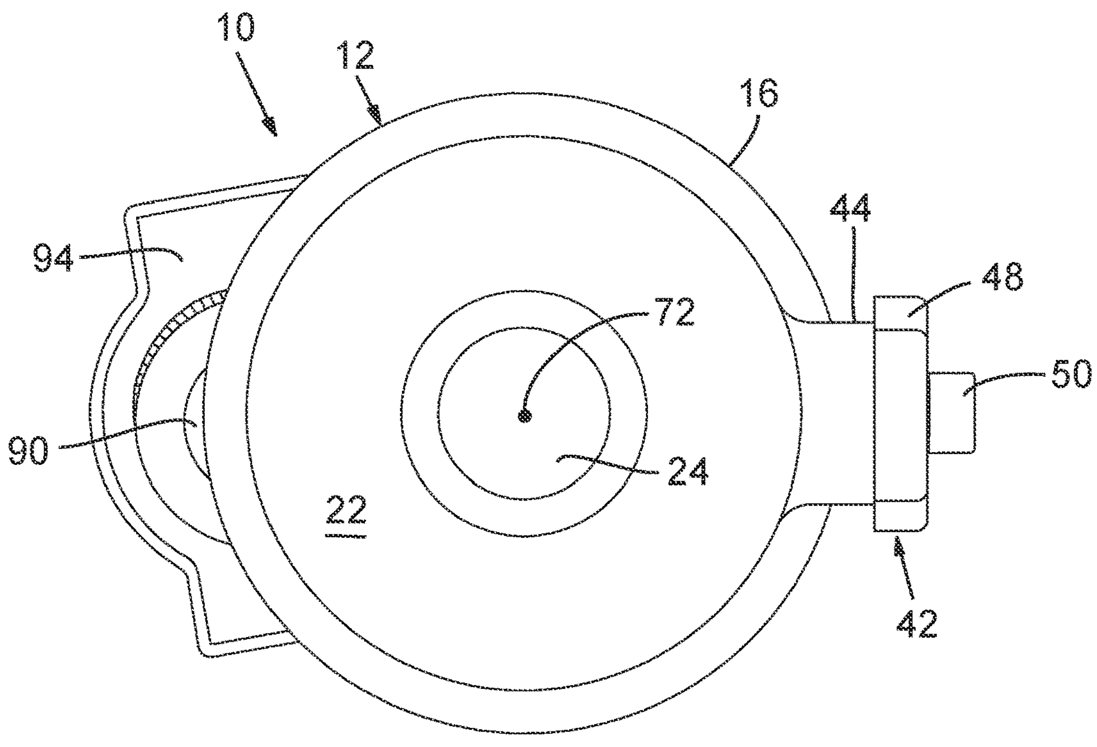
FIG. 5 is a bottom plan view of the ventilator of FIG. 1.
Figure 6:
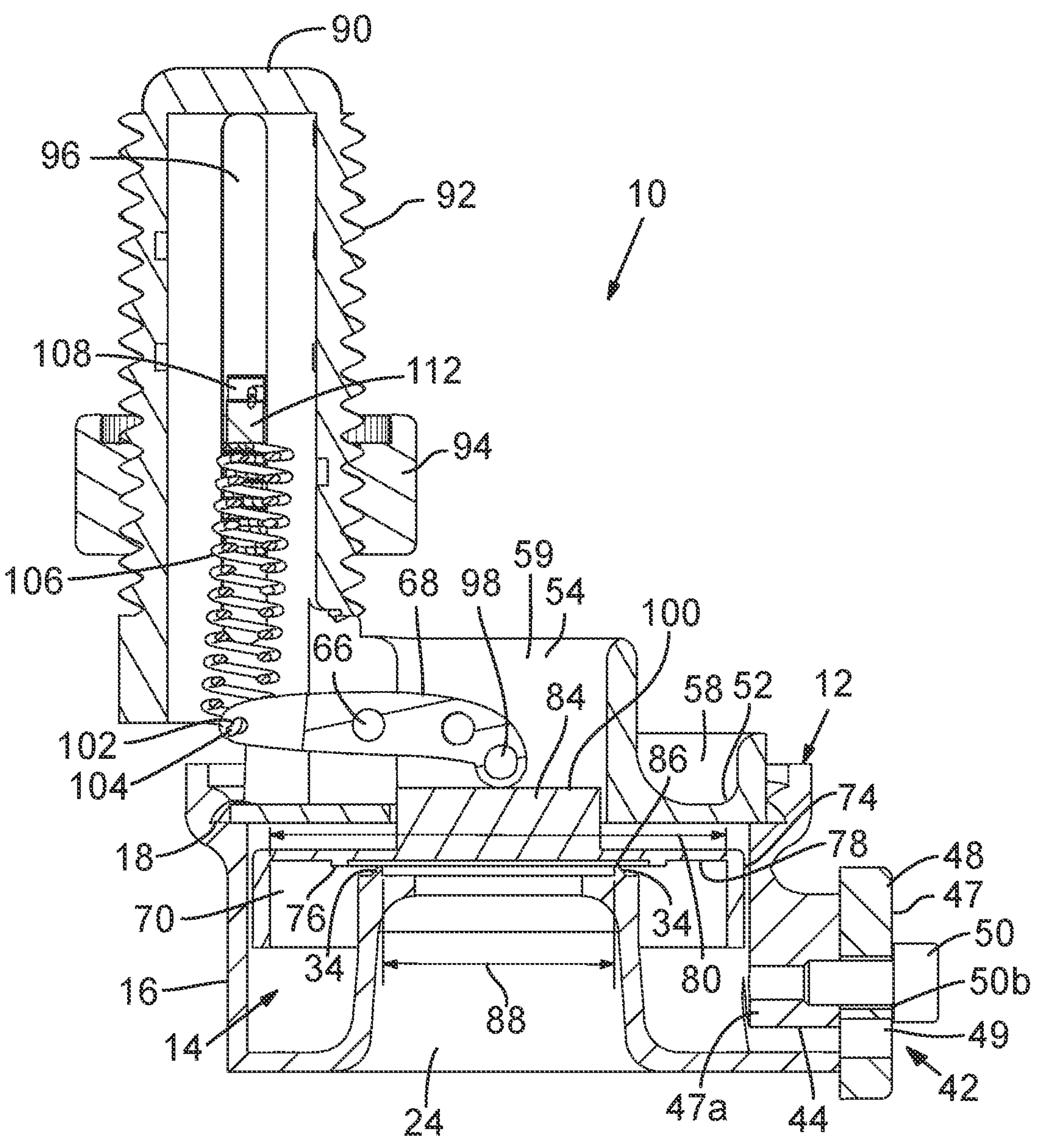
FIG. 6 is a sectional view taken along lines 6-6 of FIG. 1.
Figure 7:
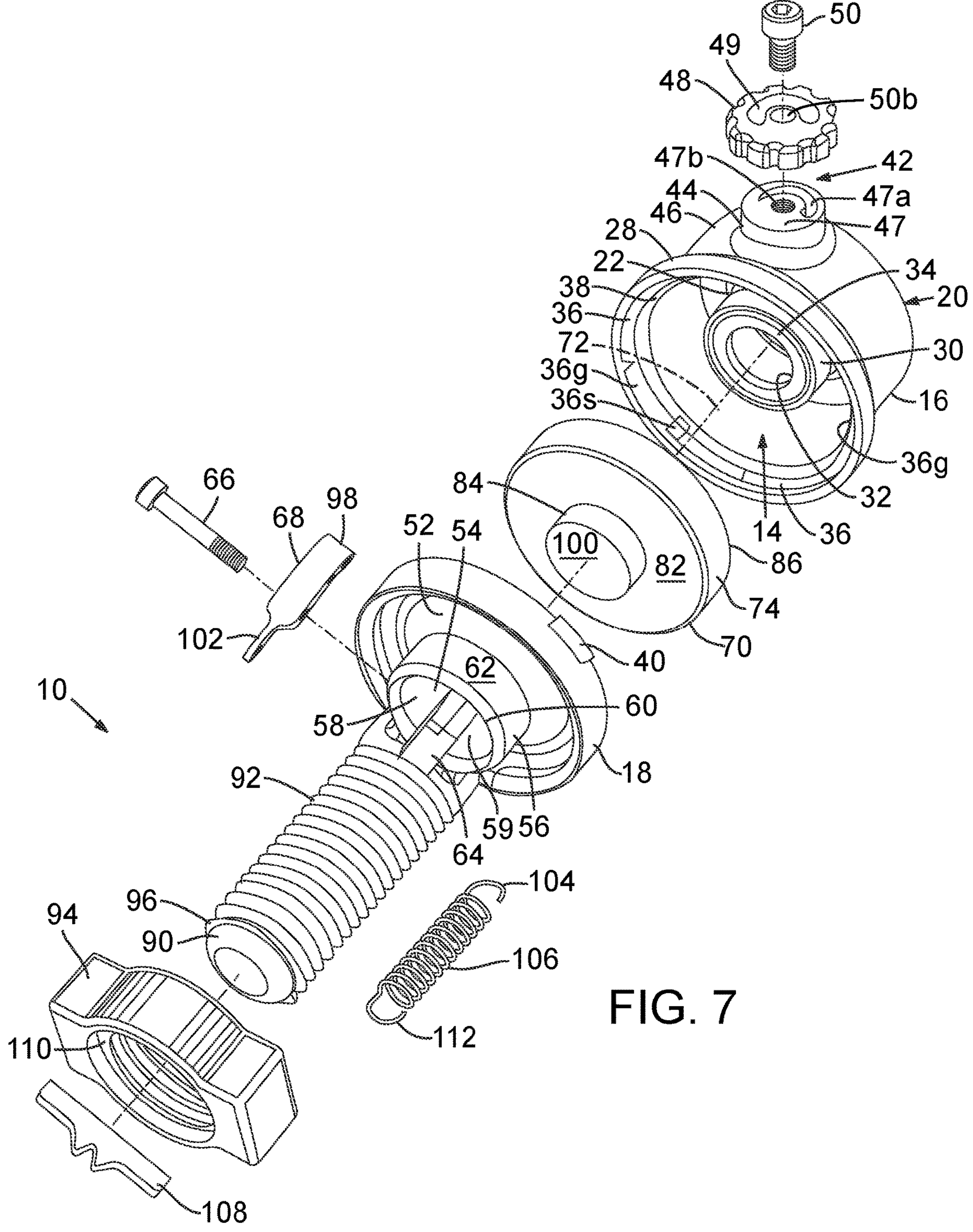
FIG. 7 is an exploded view of the ventilator of FIG. 1.

FIGS. 1-7 show various views of the disclosed gas-driven, pressure-regulated ventilator 10 configured in a first embodiment. Ventilator 10 includes a hollow valve body 12 that is of generally cylindrical shape, has an interior 14, and includes a base portion 16 and a detachable pressure adjustment portion 18.

Base portion 16 is of generally cylindrical shape and includes, at a gas inlet end 20, an annular base floor 22 having a central gas inlet opening 24 and, at a pressure adjustment portion receiving end 26, a one-quarter turn threaded flange 28.

A tubular member 30 having an opening defined by an inner wall 32 of the same size as that of central gas inlet opening 24 extends upright from base floor 22 into interior 14 of valve body 12 and terminates in a sealing rim 34 at a free end. Sealing rim 34 is set below threaded flange 28 of base portion 16.

Flange 28 includes two spaced-apart arcuate thread segments 36 that are separated by gaps 36*g* and are angularly inclined toward base floor 22. Thread segments 36 terminate in respective stop members 36*s* formed on a circumferential internal ridge 38 of base portion 16. Thread segments 36 and internal ridge 38 combine to make a channel and thereby form a first locking feature. Diametrically opposite locking tabs 40 extending from pressure adjustment portion 18 form a second locking feature. Locking tabs 40 fit in corresponding gaps 36*g* and slide between thread segments 36 and internal ridge 38 as a user twists pressure adjustment portion 18 one-quarter turn to lock it in place against stop members 36*s*.

A variable orifice valve 42 includes a neck 44 that is formed in and extends away from a side wall 46 of base portion 16 and terminates in a dial mounting surface 47. Dial mounting surface 47 has a centrally positioned screw reception bore 47*b* extending into neck 44 and a tapered arcuate gas outlet opening 47*a* extending through neck 44 and into interior 14 of valve body 12. A flow control dial 48 having an arcuate slot 49 that adjusts the flow of gas out of interior 14 of valve body 12 through tapered arcuate gas outlet opening 47*a*. Flow control dial 48 is rotatably connected to dial mounting surface 47 by a mounting screw 50 passing through a mounting bore 50*b* and engaging screw reception bore 47*b* on dial mounting surface 47 of neck 44.

Pressure adjustment portion 18 includes a pressure adjustment portion floor 52 having a central opening 54. A tubular member 56 having an opening defined by an inner wall 58 of the same size as that of central opening 54 stands upright and terminates in a free end rim 60. The interior of tubular member 56 within inner wall 58 provides a pressure adjustment open space 59. Tubular member 56 has a side wall 62 that is partly open by a lengthwise slot 64 terminating above pressure adjustment portion floor 52. A pivot pin 66 passing through both sides of slot 64 in side wall 62 supports a spring-actuated member 68, which is described in greater detail below.

A gas-pressure responsive displacement member or piston 70 configured in the form of a cup is contained within interior 14 of valve body 12 and is sized for movement in either direction along a longitudinal axis 72 of valve body 12. Piston 70 has a circumferential side wall 74 and a bottom 76 that is bounded by an interior surface 78 having a first circular surface area 80 (indicated by its diameter in FIG. 6) and an exterior surface 82. A circular boss 84 extending away from exterior surface 82 is sized to fit through central opening 54 in pressure adjustment portion floor 52 and within pressure adjustment open space 59. A raised elastomeric seal 86 is affixed to interior surface 78 and is sized so that it makes continuous contact with sealing rim 34 when piston 70 rests against tubular member 30 of base portion 16 in the absence of gas flow into valve body 12. A second circular surface area 88 (indicated by its diameter in FIG. 6) is delineated by the area circumscribed by sealing rim 34 when raised elastomeric seal 86 on inner surface 78 of piston 70 rests against tubular member 30.

A spring support member or upstanding tubular post 90 is formed as part of pressure adjustment portion 18, located at its rim 60. Post 90 has a threaded outer surface 92 for threaded engagement with a spring tension adjustment nut 94 and two diametrically opposite lengthwise slots 96. Spring-actuated arm 68 is pivotally mounted to tubular member 56 by pivot pin 66. Spring-actuated arm 68 has a distal end 98 that extends into pressure adjustment open space 59 and applies a force against a contact surface 100 of boss 84. Spring-actuated arm 68 has a spring connection tab 102 that extends into the interior of post 90 and is connected to one end 104 of a spring 106 contained in post 90. A spring hanger support bar 108 extending through slots 96 rests against a circumferential internal ridge 110 of spring tension adjustment nut 94 and supports an opposite end 112 of spring 106. Spring 106 is of an extension spring type; therefore, spring-actuated arm 68 always applies force against contact surface 100 of boss 84.

Rotating spring tension adjustment nut 94 in a clockwise direction lowers hanger support bar 108 toward pressure adjustment portion 18 and thereby relaxes spring 106 to decrease the amount of force applied to contact surface 100 of boss 84. Similarly, rotating spring tension adjustment nut 94 in a counterclockwise direction raises hanger support bar 108 away from pressure adjustment portion 18 and thereby stretches spring 106 to increase the amount of force applied to contact surface 100 of boss 84.

Figures 8A, 8B:
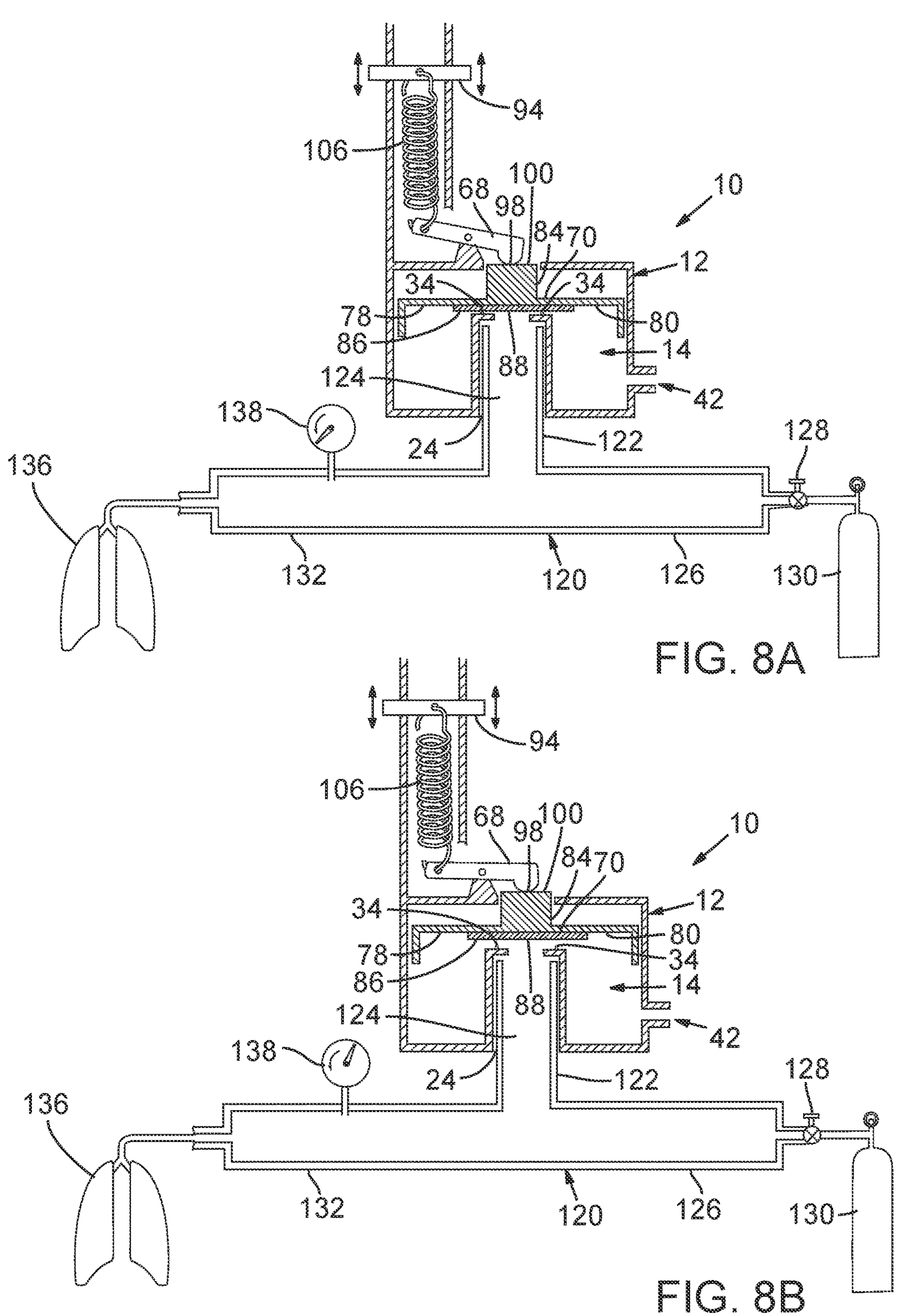
FIGS. 8A and 8B are schematic diagrams of the disclosed ventilator, which is shown partly in cross section to demonstrate its operation and use in, respectively, closed and open configurations.

FIGS. 8A and 8B show schematic representations of ventilator 10 to further illustrate its operating principle and use. In these schematics, a tee-adapter 120 is used in conjunction with ventilator 10 to establish a flow circuit to demonstrate gas flow paths during inhalation-exhalation breath cycles. Tee-adapter 120 comprises a first tee-branch 122 inserted into central opening 24 of valve body 12 to establish a breathing gas pathway 124; a second tee-branch 126 connected to a gas inlet 128 in communication with a pressurized gas source 130, the gas inlet adjustable to supply breathing gas at a prescribed constant rate of flow into tee-adapter 120; and a third tee-branch 132 to convey gas flow to and from lungs 136 of a patient to effect cyclic mechanical ventilation (i.e., cyclic inhalation and exhalation).

FIG. 8A shows ventilator 10 in a closed configuration with piston 70 positioned such that raised elastomeric seal 86 on interior surface 78 rests atop sealing rim 34 to prevent pressurized gas in breathing gas pathway 124 from entering interior 14 of valve body 12. In this closed configuration, distal end 98 of spring-loaded arm 68 exerts on contact surface 100 of circular boss 84 of piston 70 a downward force that is greater than the upward force exerted by gas pressure within breathing gas pathway 124 acting over second surface area 88, thereby maintaining the position of piston 70 in contact with sealing rim 34. The magnitude of this downward force may be increased or decreased by moving spring tension adjustment nut 94 up or down to lengthen or shorten, respectively, spring 106, thereby adjusting the desired PIP value to be maintained by ventilator 10 during mechanical ventilation. With piston 70 in this closed position, the flow of gas entering tee-adapter 120 at a constant rate through gas inlet 128 from pressurized gas source 130 is directed into patient's lungs 136, causing them to expand as gas is introduced (i.e., inhalation). As patient's lungs 136 expand, gas pressure within tee-adapter 120 increases—as depicted on pressure gauge 138 in FIG. 8A—and, accordingly, the upward force exerted by gas pressure acting over second surface area 88 also increases.

Once the gas pressure in tee-adapter 120 has increased sufficiently that the upward force of the gas pressure acting over second surface area 88 matches, then exceeds, the downward force exerted by distal end 98 of spring-loaded arm 68 on circular boss 100 of piston 70 (i.e., gas pressure has reached the set PIP value), the continuous contact between raised elastomeric seal 86 and sealing rim 34 is breached. This breach allows the pressurized gas in tee-adapter 120 to enter valve body 12 and exert an upward force acting over first surface area 80 of interior surface 78 of piston 70. The exertion of gas pressure over the larger first surface area 80 substantially increases the upward force acting in opposition to the downward force exerted by spring-loaded arm 68, causing piston 70 to move to the open position shown in FIG. 8B. In this configuration, the flow of gas within tee-adapter 120 is re-directed through breathing gas pathway 124 into interior 14 of valve body 12 and exhausted through variable orifice valve 42. As gas is exhausted from valve body 12, the gas pressure within tee-adapter 120 decreases, as depicted on pressure gauge 138 in FIG. 8B. Concomitantly with the falling gas pressure, breathing gas from lungs 136 is exhaled into tee-adapter 120 and is directed through breathing gas pathway 124 into interior 14 of valve body 12 and exhausted through variable orifice valve 42 as lungs 136 return to their pre-expansion state.

When the gas pressure in tee-adapter 120 has fallen sufficiently, the downward force exerted by distal end 98 of spring-loaded arm 68 on contact surface 100 of circular boss 84 causes piston 70 to return to the closed position of FIG. 8A, thereby blocking further flow of gas into valve body 12 for exhaust through variable orifice valve 42. At this point, the continuous inflow of breathing gas from gas inlet 128 causes re-pressurization to resume in tee-adapter 120 and inhalation of breathing gas into lungs 136, thus initiating a new breath cycle.

Ventilator 10 is designed to allow a clinician to adjust the magnitude of PIP and PEEP values and the duration of inhalation and exhalation flows in a breath cycle to accommodate patient-specific ventilation needs. The PIP and PEEP values are related through the ratio between first surface area 80 of interior surface 78 of piston 70 and second surface area 88 (i.e., the area circumscribed by sealing rim 34). First surface area 80 and second surface area 88 are the surface areas over which the gas pressure in breathing gas pathway 124 acts to exert an upward force on piston 70 when it is in the open and closed positions, respectively. Thus, once a PIP value is set, the PEEP value is also set.

In practice, a PIP is set to a desired value by adjusting the tension of spring 106 to increase or decrease the amount of downward force that distal end 98 of spring-loaded arm 68 applies to piston 70 to maintain it in the closed position. This PIP value reflects the maximum gas pressure that can be sustained in breathing gas pathway 124 before the seal between raised elastomer seal 86 and sealing rim 34 is breached and piston 70 moves to the open position. The corresponding PEEP value is then determined, to a first order, according to:

$$PEEP = \frac{\text{second surface area}}{\text{first surface area}} * PIP$$

The duration of inhalation and exhalation in a given breath cycle can be adjusted by the clinician to achieve the desired breathing frequency or breaths-per-minute during mechanical ventilation by changing the rate of gas inflow and gas outflow from the system. The duration over which an inhalation occurs is controlled by adjusting rate of inflow of gas from pressurized gas source 130 at gas inlet 128. This rate of inflow of gas controls the rate at which patient's lungs 136 inflate and the rate at which pressure rises in breathing gas pathway 124 before reaching the set PIP value and forcing piston 70 from the closed position to the open position. Thus, a higher rate of inflow of gas into tee-adapter 120 will cause piston 70 to be forced from the closed position to the open position in a shorter amount of time, effectively decreasing the inspiration duration during a breath cycle. Conversely, a lower rate of gas flow into tee-adapter 120 will lengthen the amount of time that is taken for piston 70 to be pushed from the closed position to the open position, increasing the inspiration duration during a breath cycle.

The duration over which an exhalation occurs is controlled by adjusting flow control dial 48 of variable orifice valve 42 to change the outflow resistance as gas is exhausted from interior 14 of valve body 12 when piston 70 in the open position. This adjustment controls the rate of exhalation of gas from patient's lungs 136 and the rate at which gas pressure falls in breathing gas pathway 124 as it returns to the set PEEP value and piston 70 returns to the closed position. Thus, a higher rate of outflow of gas from variable orifice valve 42 will cause piston 70 to be return to the closed position in a shorter amount of time, effectively decreasing the exhalation duration during a breath cycle. Conversely, a lower rate of gas flow from variable orifice valve 42 will lengthen the amount of time that is taken for piston 70 return to the closed position, increasing the inspiration duration during a breath cycle.

Figure 9:
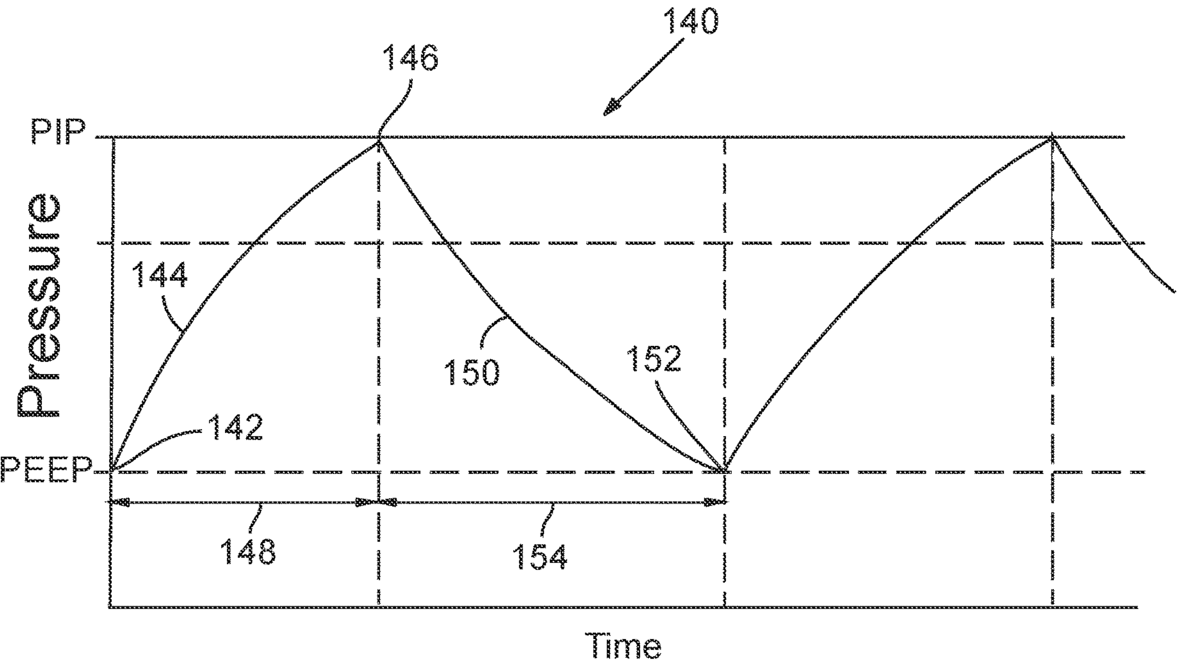
FIG. 9 is an exemplary plot of gas pressure versus time during a breath cycle, including inhalation followed by exhalation, under control of an embodiment of the disclosed ventilator.

FIG. 9 shows an exemplary plot of gas pressure versus time during a breath cycle 140 including inhalation followed by exhalation under control of ventilator 10. Breath cycle 140 begins with the gas pressure in breathing gas pathway 124 at a desired minimum pressure value 142 at inhalation (i.e., the PEEP value set by the clinician) and piston 70 in the closed position. As gas pressure increases in breathing gas pathway 124 along pressure rise 144, inhalation of breathing gas into patient's lungs 136 takes place until a desired maximum pressure value 146 is reached (i.e., the PIP value set by the clinician), at which point piston 70 moves to the open position. The rate of pressure increase along pressure rise 144 determines an inhalation duration 148 for breath cycle 140. With piston 70 now in the open position, gas pressure in breathing gas pathway 124 decreases along pressure fall 150, causing exhalation of breathing gas from patient's lungs 136 until a minimum pressure value 152 at exhalation is reached (i.e., the set PEEP value, which is the same value as minimum pressure value 142 at inhalation), at which point piston 70 returns to the closed position. The rate of pressure decrease along pressure fall 150 determines an exhalation duration 154 for breath cycle 140. The total duration of breath cycle 140 is the sum of inhalation duration 148 and exhalation duration 154.

FIGS. 10A, 10B, 10C, 10D, 10E, 10F, 10G, 10H, and 11 show various views of the disclosed gas-driven, pressure-regulated ventilator 210 configured in a second embodiment. Ventilator 210 includes a hollow valve body 212 that is of generally cylindrical shape, has an interior 214 (FIGS. 10G, 10H, 11, 12A), and includes a base portion 216 and a detachable pressure adjustment portion 218 (FIGS. 10G, 10H, 11, 13A, 13B).

Figure 11:
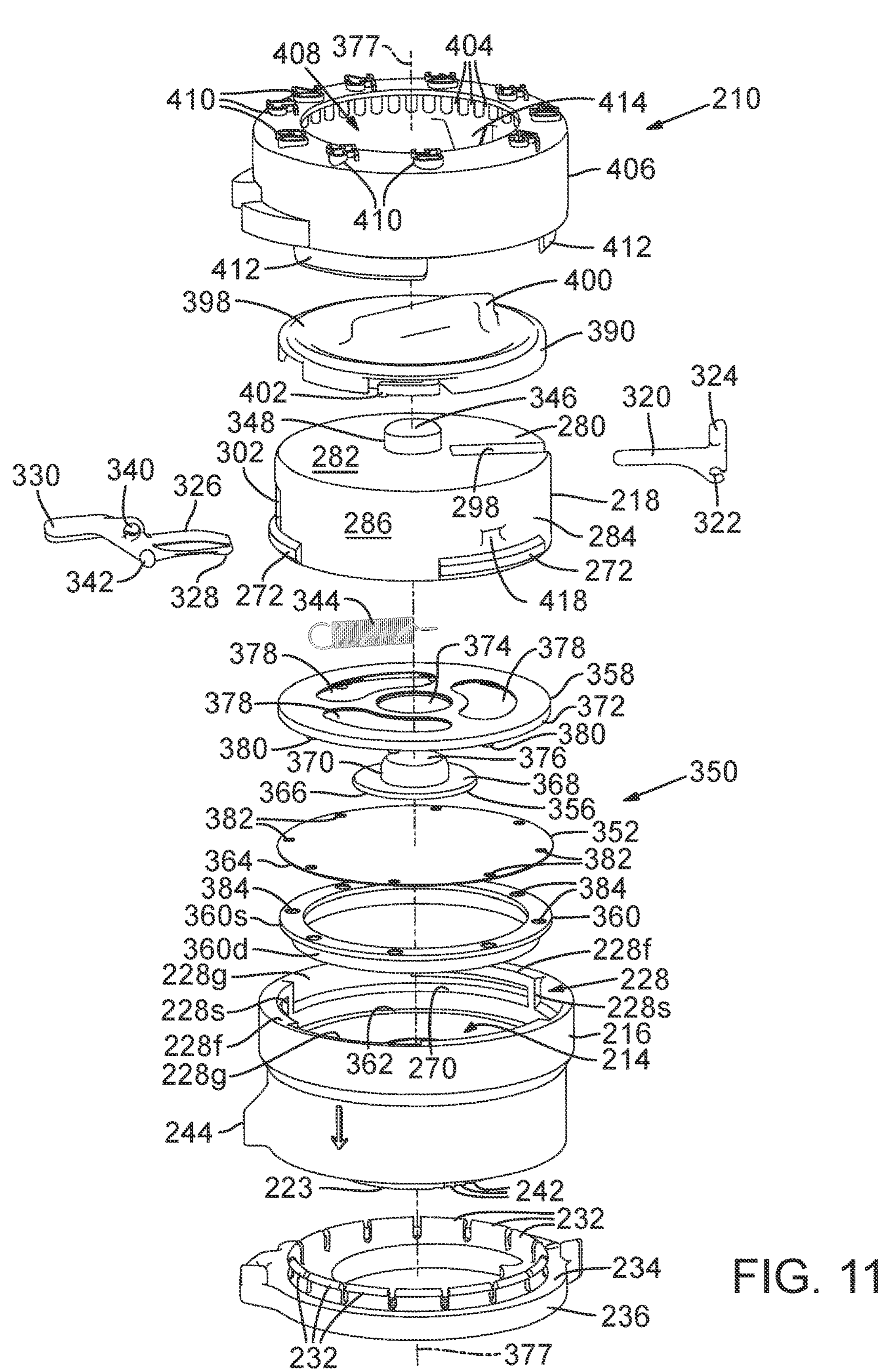
FIG. 11 is an exploded view of the ventilator of FIGS. 10A-10F.
Figure 12A:
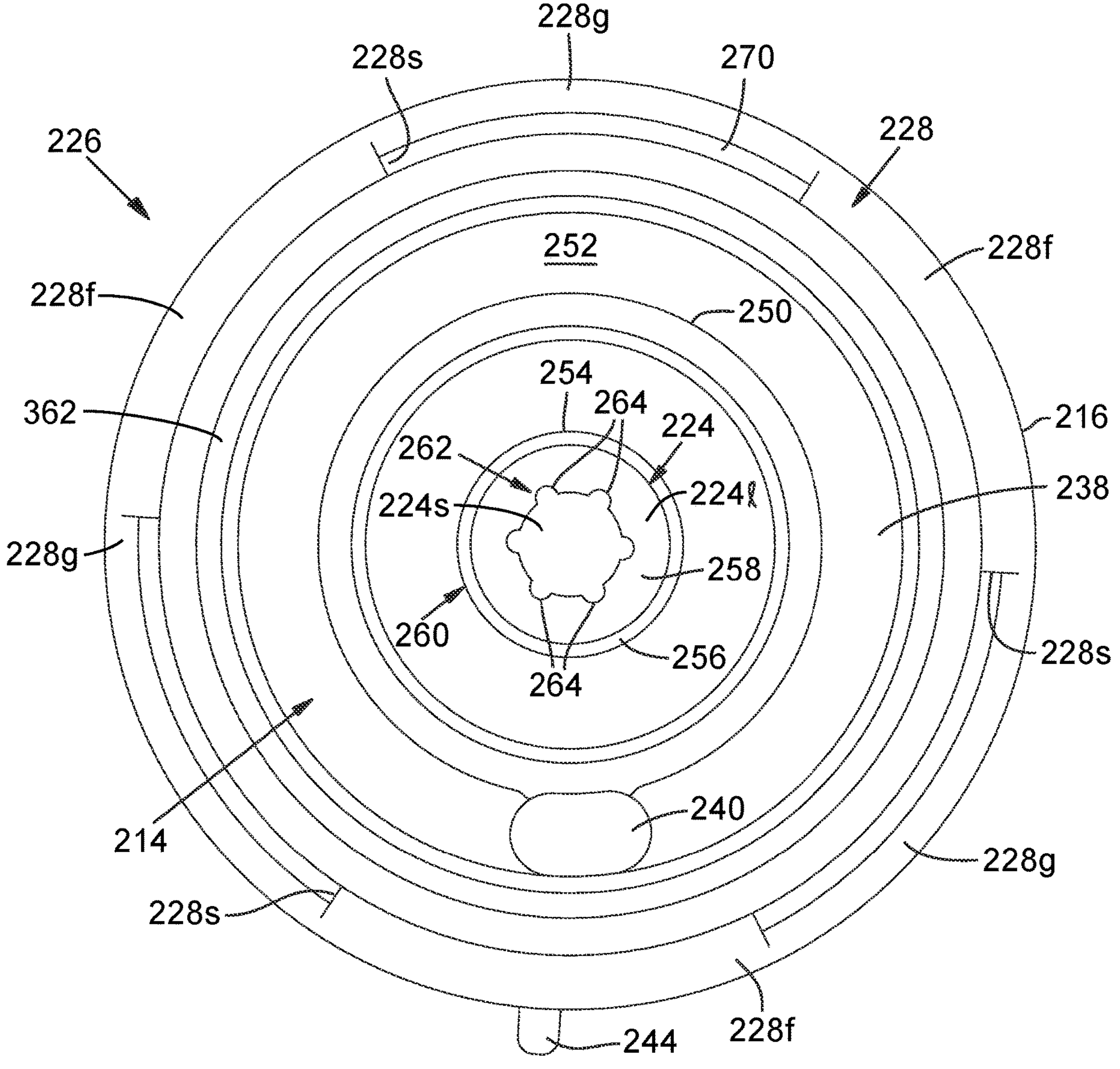
FIGS. 12A and 12B are, respectively, top plan interior and bottom plan exterior views of a base portion of the ventilator of FIGS. 10A-10F.
Figure 12B:
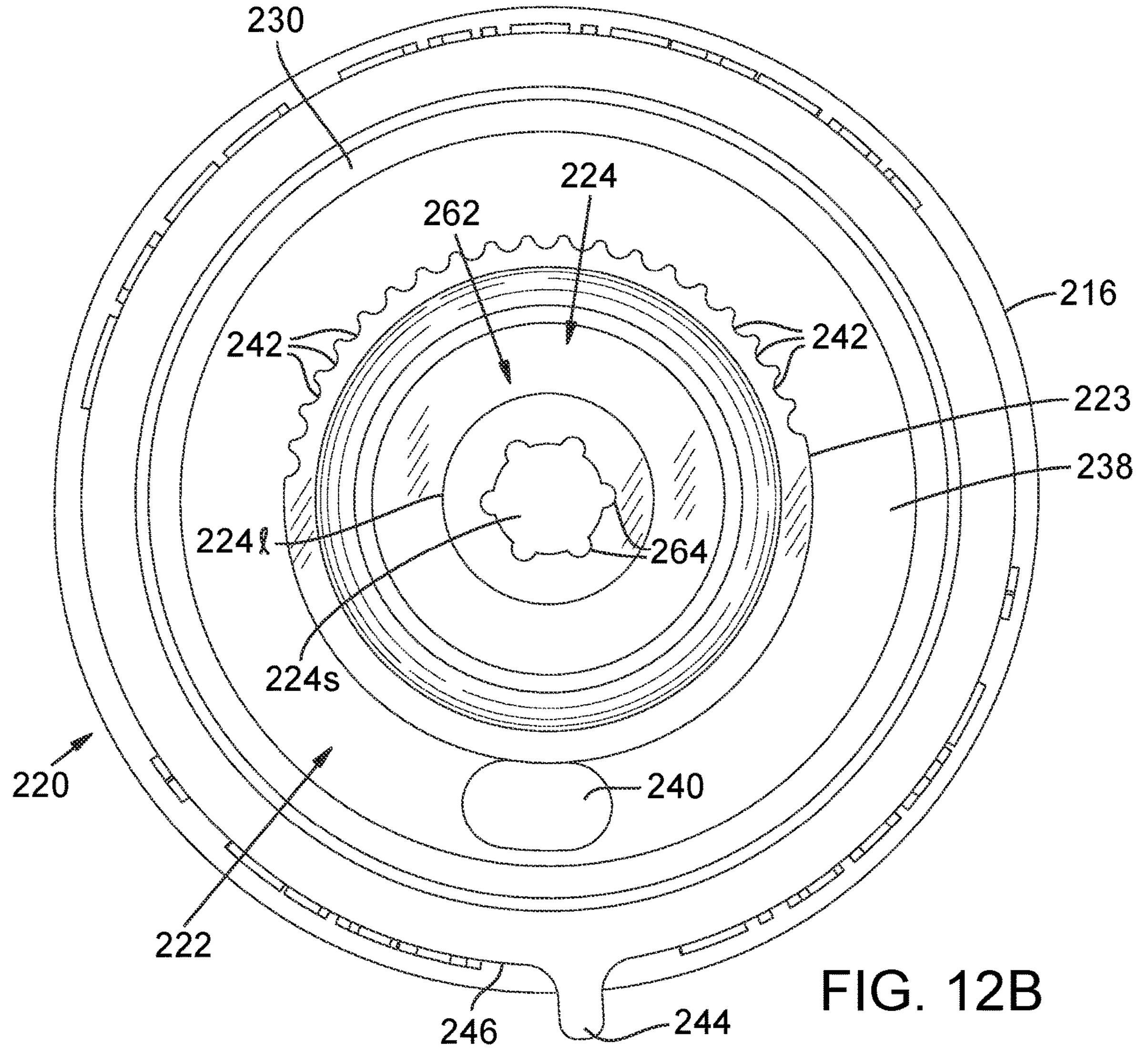

With particular reference to FIGS. 11, 12A, and 12B, base portion 216 is of generally cylindrical shape and includes, at a gas inlet end 220, a recessed base floor 222 having a stepped central gas inlet opening 224 that is bounded by an outwardly extending circular section 223. Central gas inlet opening 224 includes a larger diameter circular central opening 2241 and a concentric smaller diameter circular central opening **224*s* and, at a pressure adjustment portion-receiving end 226, a one-sixth turn segmented flange 228. The area defined by central opening 2241 is greater than that of central opening 224*s***.

Base floor 222 includes near the perimeter of base portion 216 a circumferential groove 230 that receives spaced-apart tabs 232 circumferentially arranged near the perimeter of an interior surface 234 of a gas flow rate selector dial 236, which operates in the manner described below. An annular base section 238 bounded by groove 230 in, and outwardly extending circular section 223 of, base portion 216 includes a gas outlet opening or through-hole 240. A set of spaced-apart rate selector dial indexing slots 242 is formed in the outer surface of circular section 223 in an approximately 180° arc at a region opposite the location of through-hole 240. A rate selector dial stop member 244 projects from a side wall 246 of base portion 216 at inlet end 220.

A tubular member 250 extends upright from an inner surface 252 of annular base section 238 into interior 214 of base portion 216 of valve body 212 and terminates in a sealing rim 254 at a free end. Sealing rim 254 is set below segmented flange 228 of base portion 216. Tubular member 250 has an interior recess 256 that extends, in a direction toward inner surface 252, from sealing rim 254 to an annular floor 258 in which central opening **224*s* is formed. Sealing rim 254 defines a central opening 260 having a diameter that is greater than that of central opening 224*s* and sets a parameter that is used to set the PIP value of ventilator 210. Central opening 224*s* constitutes part of an orifice plate 262 that has notches 264 formed in the periphery of central opening 224*s*. Each of notches 264 introduces localized turbulent air flow contributing to an average air turbulence that breaks up a laminar air cushion to make a more stable patient breath cycle. Orifice plate 262 may be formed in annular floor 258 as an integral part of tubular member 250 or be formed as a separate component part configured to be set against recessed base floor 222 and inserted into central opening 2241 to a point below sealing rim 254**.

Segmented flange 228 includes three spaced-apart arcuate flange segments **228*f* that are separated by gaps 228*g*. Flange segments 228*f* terminate in respective stop members 228*s* formed on a circumferential internal ridge 270 of base portion 216. Flange segments 228*f* and internal ridge 270 combine to make a channel and thereby form a first locking feature. Locking tabs 272 mutually angularly spaced-apart by 120° extend from pressure adjustment portion 218 to form a second locking feature. Locking tabs 272 fit in corresponding gaps 228*g* and slide between flange segments 228*f* and internal ridge 270 as a user rotates pressure adjustment portion 218 one-sixth turn to lock it in place against stop members 228*s***.

Figures 13A, 13B:
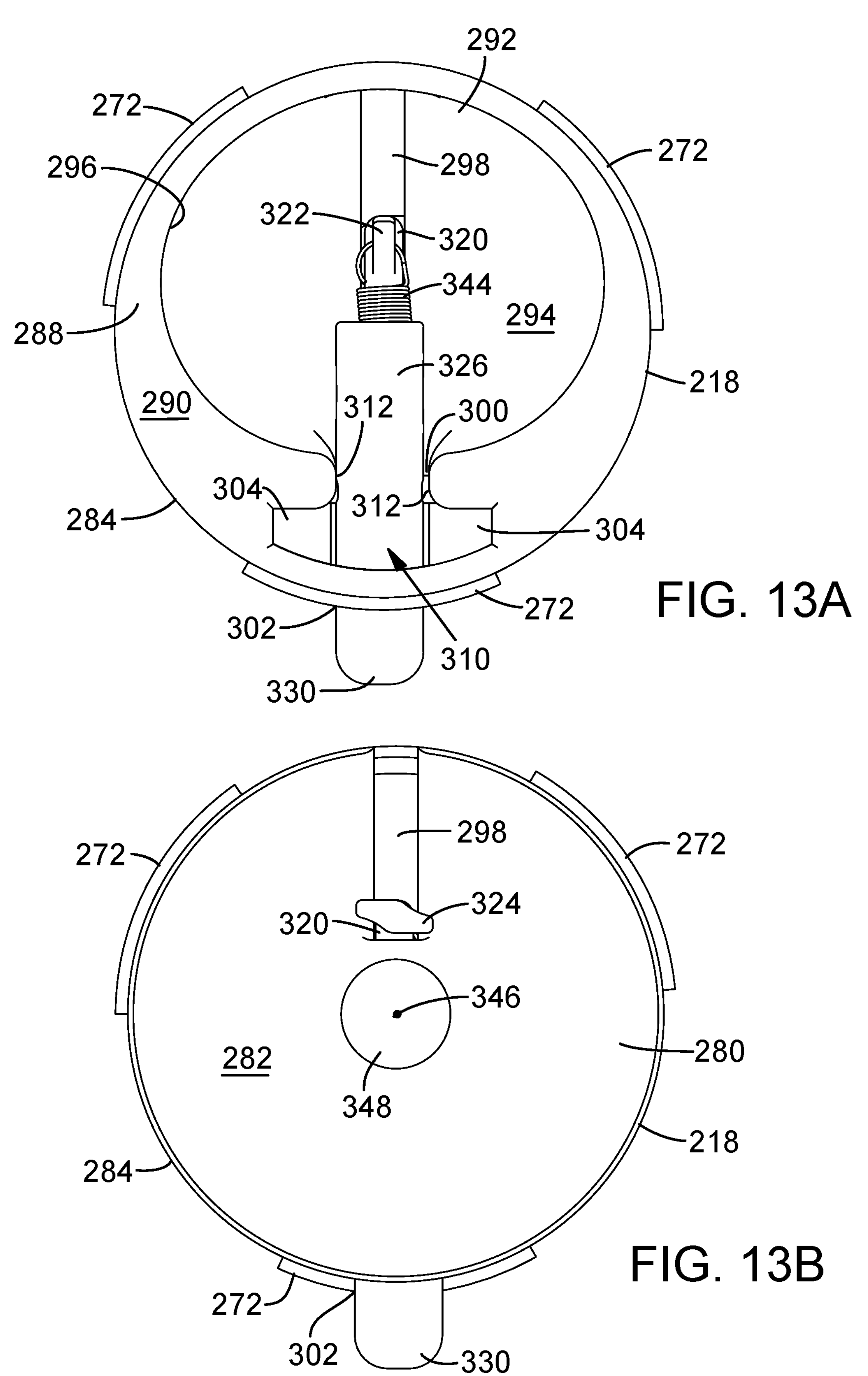
FIGS. 13A and 13B are, respectively, bottom plan interior and top plan exterior views of a detachable pressure adjustment portion of the ventilator of FIGS. 10A-10F.

With particular reference to FIGS. 11, 13A, and 13B, pressure adjustment portion 218 is of circular shape and is formed of a top wall 280 having a surface 282, a side wall 284 having a surface 286, and a primarily open bottom wall 288 having a surface 290. An oval-shaped pressure adjustment open space 292 formed in the interior of pressure adjustment portion 218 is bounded by a floor 294 and a partly open inner side wall 296. A rectangular guide slot 298 provided in top wall 280 forms a rectangular opening extending between surface 282 and floor 294. A rectangular gap 300 provided from surface 290 to floor 294 in inner side wall 296 and a rectangular opening 302 extending from inner side wall 296 and through side wall 284 form a passageway from surface 286 and into open interior space 292. Two spaced-apart shoulder portions 304 formed on either side of opening 302 in side wall 284 are set below surface 290 of bottom wall 288. A T-shaped opening 310 in bottom wall 288 provides two spaced-apart U-shaped pivot pin catches 312, each formed by an interior surface portion of inner side wall 296 at rectangular gap 300, joining the spatially aligned portion of bottom wall 288 and shoulder portion 304.

A spring support member comprising a spring tension slider 320 has at a distal end a spring attachment eyelet 322 and a spring tension adjustment support cam 324. Spring attachment eyelet 322 extends into pressure adjustment open space 292. Spring tension adjustment support cam 324 is longer than the width of rectangular guide slot 298 and is configured to slide along surface 282 of top wall 280. A spring-actuated member comprising a lever arm 326 has at one end a membrane frame-contacting surface 328 that extends into pressure adjustment open space 292 and at the opposite end a manual backup tab 330 that extends outwardly from rectangular opening 302. Lever arm 326 has between its ends a central portion that includes a spring attachment eyelet 340 and two pivot pins 342 (one shown in FIG. 11) that extend laterally from either side of lever arm 326. Pivot pins 342 are configured to fit into spatially aligned pivot pin catches 312.

An extension spring 344 is connected to spring attachment eyelets 322 and 340. When at rest, extension spring 344 pulls pivot pins 342 into pivot pin catches 312 and spring tension adjustment support cam 324 against the end of rectangular guide slot 298 in top wall 280, nearer to its center 346. A spring tension adjustment lid central locating pin 348 extends outwardly from surface 282 of top wall 280 at its center 346.

Figure 13C:
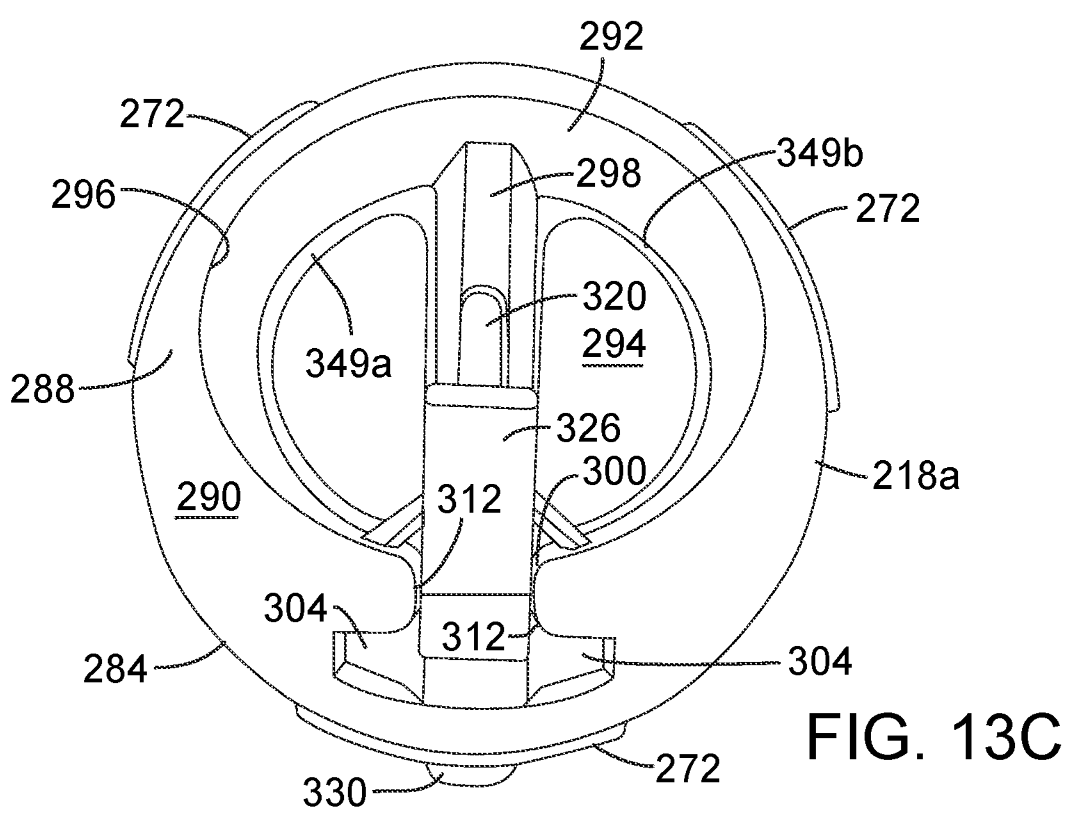
FIGS. 13C and 13D are, respectively, bottom plan interior and top plan exterior views of an alternative embodiment of a detachable pressure adjustment portion of the ventilator of FIGS. 10A-10F.
Figure 13D:
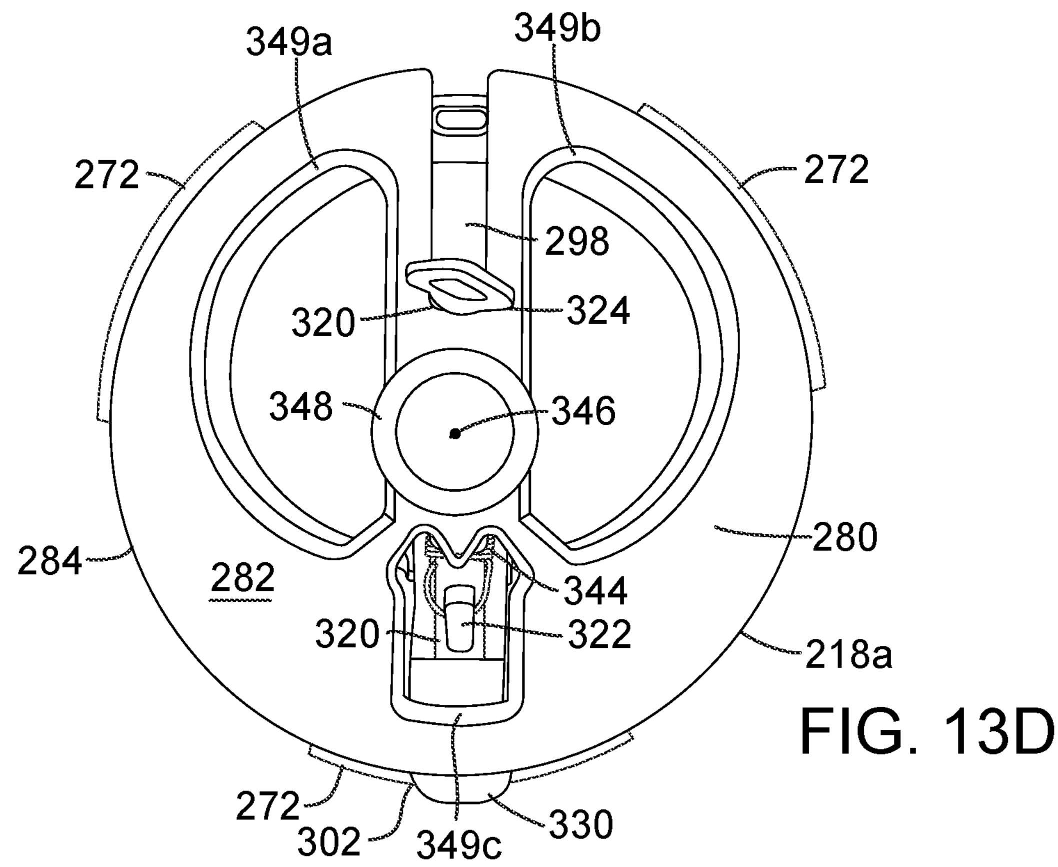

FIGS. 13C and 13D show an alternative embodiment of a pressure adjustment portion 218*a*, wherein excess material is removed from top wall 280. Removal of this excess material produces a set of three cut-outs, 349*a*, 349*b*, and 349*c*, that pass through top wall 280. Cut-outs 349*a*, 349*b*, and 349*c* decrease the amount of material needed to manufacture pressure adjustment portion 218*a* without compromising the structural integrity of the component. Cutouts 349*a* and 349*b* provide an additional benefit in that they facilitate insertion of pressure adjustment portion 218*a* into, or removal of pressure adjustment portion 218*a* from, base portion 216 during assembly or disassembly, respectively, using the thumb and index finger to grasp the component.

Figure 14A:
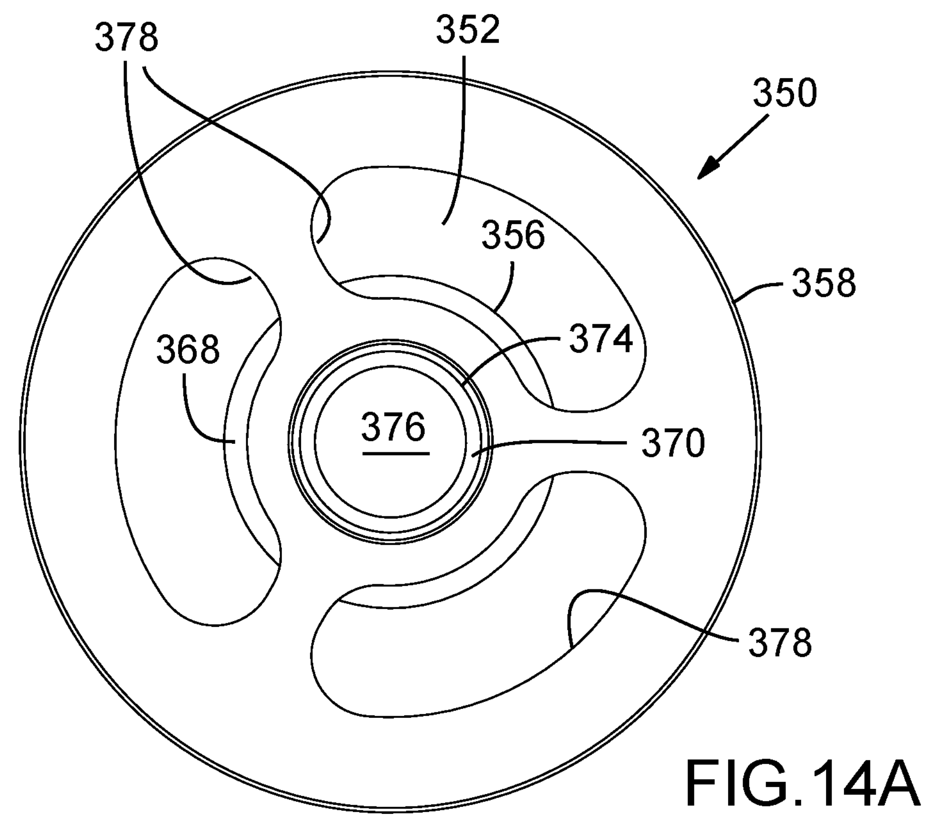
FIGS. 14A and 14B are, respectively, top plan and bottom plan views of a membrane assembly of the ventilator of FIGS. 10A-10F.
Figure 14B:
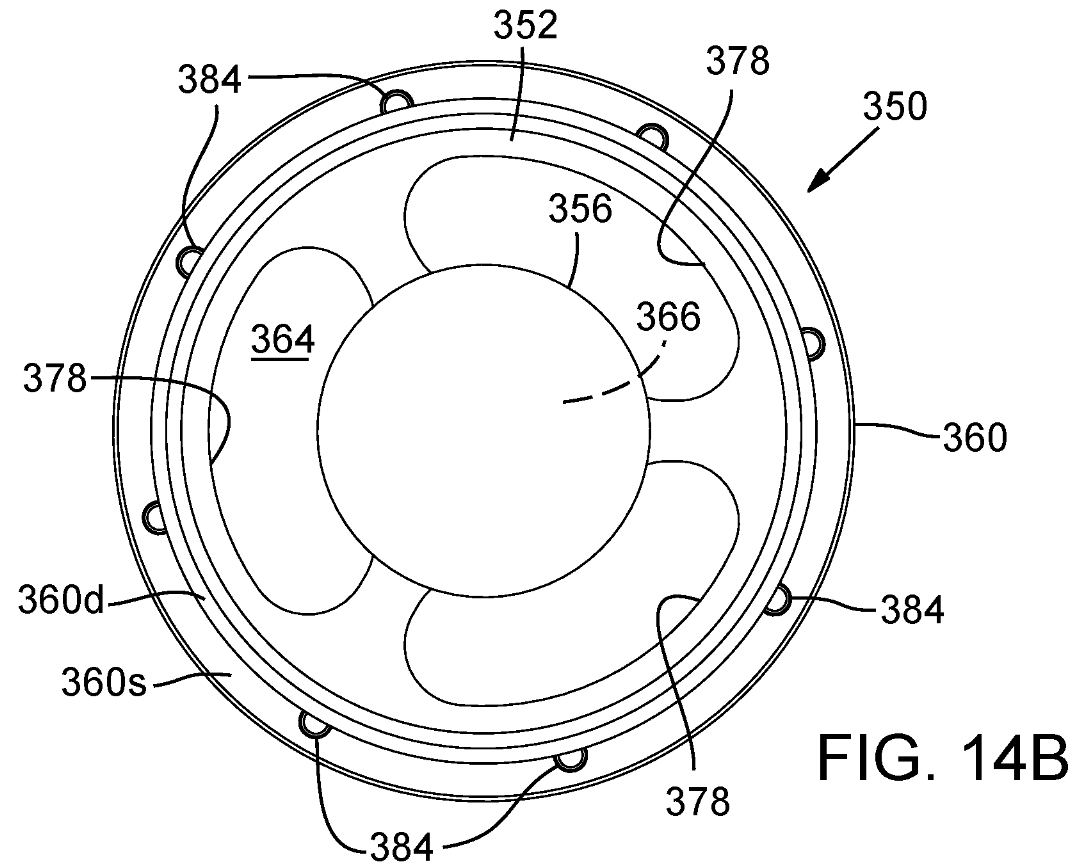
Figure 15A:
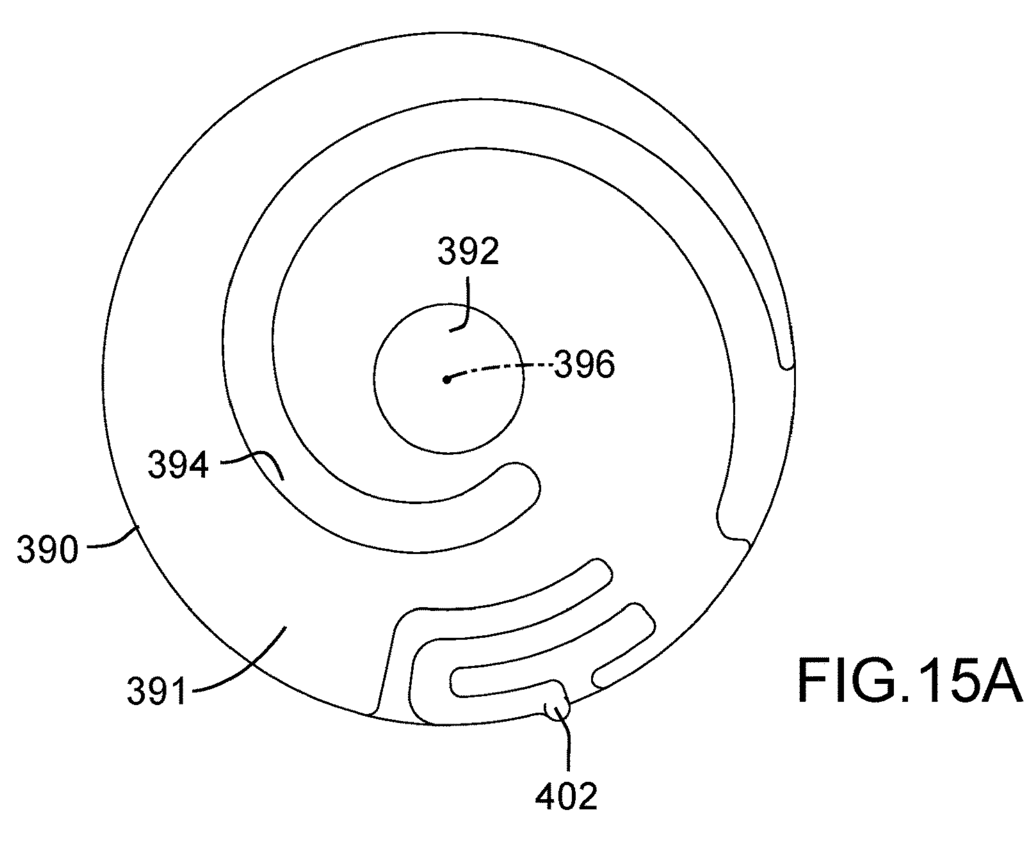
FIGS. 15A, 15B, and 15C are, respectively, bottom plan interior, side elevation, and perspective interior views of a spring tension selector lid of the ventilator of FIGS. 10A-10F.
Figure 15B:
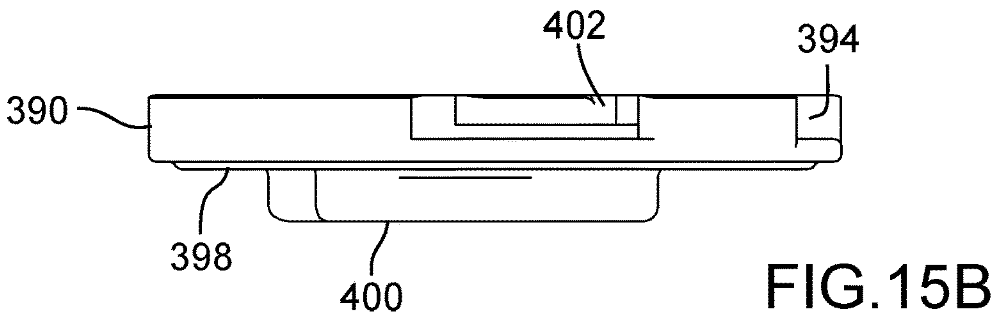
Figure 15C:
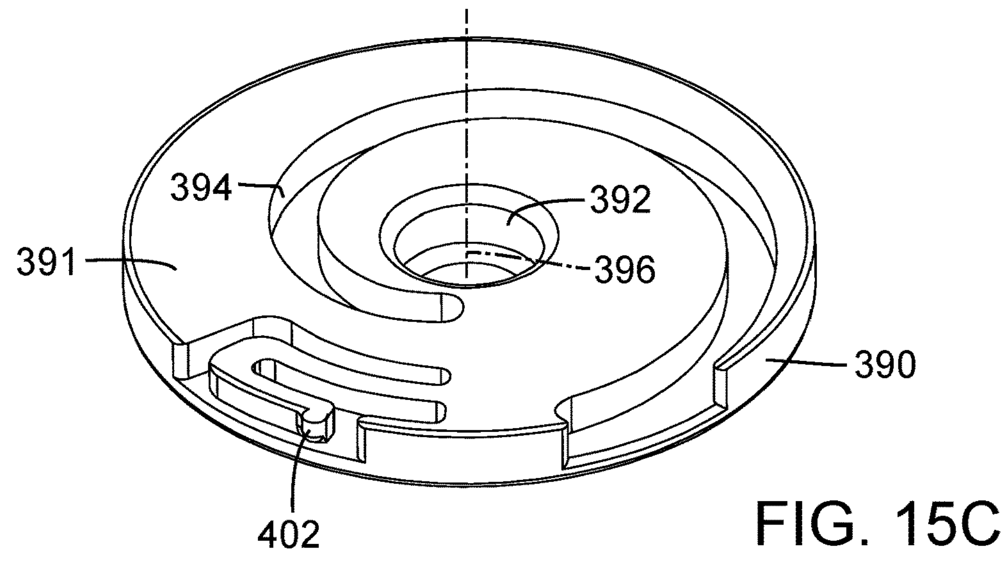
Figure 15D:
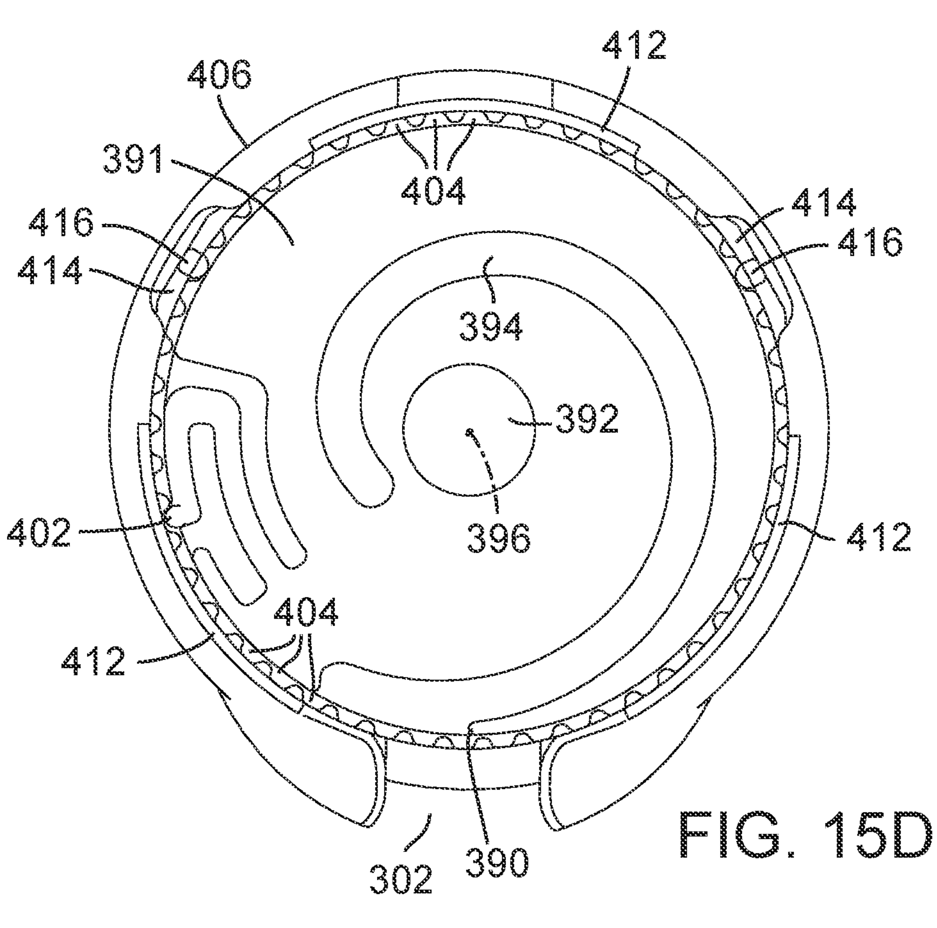
FIGS. 15D and 15E are, respectively, bottom plan interior and oblique views of the spring tension selector lid covered by a gas pressure indicating cap.
Figure 15E:
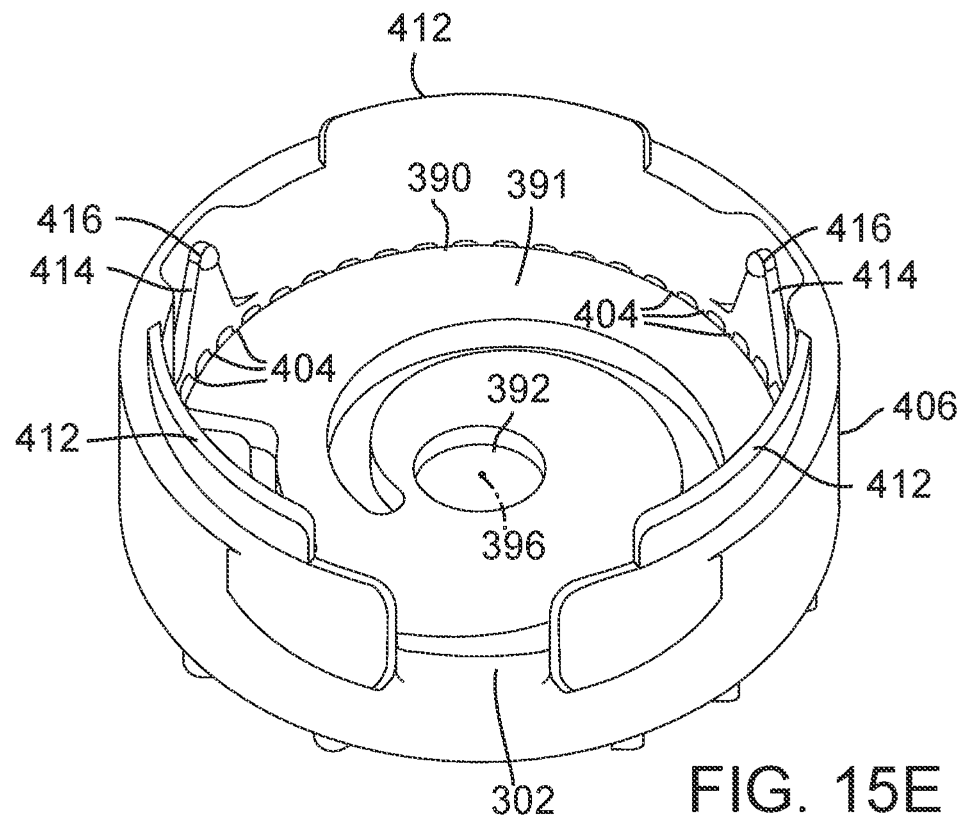

With particular reference to FIGS. 11, 14A, and 14B, a membrane assembly 350 is contained in interior 214 of base portion 216 of valve body 212. Membrane assembly 350 is formed of a membrane film 352 and a membrane force adapter 356 positioned between a membrane frame top 358 and a membrane frame bottom 360 that are adhesively or thermally bonded together. Membrane force adapter 356 is preferably in the form of a thin circular disk. Membrane frame top 358 and membrane frame bottom 360 are preferably in the form of, respectively, a thin multi-apertured circular disk and a flanged ring. Membrane film 352 is preferably an about 0.5 mm-thick sheet of USP class 6 silicone characterized by durometer Shore A hardness scale of between about 40 and about 60, with 50 being preferred. Membrane frame bottom 360 has a shoulder portion 360*s*, which is of the same diameter as that of membrane frame top 358, and a downwardly depending portion 360*d*, which has a diameter that is shorter than the inner diameter of a circumferential internal mounting rim 362 of base portion 216. When membrane assembly 350 is set in valve body 212, the bottom surface of shoulder portion 360*s* of membrane frame bottom 360 rests on internal mounting rim 362 of base portion 216. A purpose of downwardly depending portion 360*d* of membrane frame bottom 360 is to ensure that pressure adjustment portion 218 and base portion 216 cannot be properly assembled if membrane assembly 350 is placed upside down in base portion 216. Internal mounting rim 362 is located a small distance (e.g., 0.5 mm-2.0 mm, with 1.0 mm preferred) below sealing rim 254, upon which a gas-receiving surface 364 of membrane film 352 rests in absence of gas flow into valve body 212. Membrane force adapter 356 has a membrane-contacting surface 366 and an opposite surface 368 from which a circular boss 370 extends. Membrane frame top 358 has a flat membrane force adapter-contacting, membrane-facing surface 372 and a generally centrally located circular aperture 374 through which boss 370 projects. A top surface 376 of boss 370 contacts membrane frame-contacting surface 328 of lever arm 326. During a breathing cycle, membrane film 352 flexes by an amount that causes boss 370 to move about 1.33 mm along a longitudinal axis 377 of valve body 212. Three spaced-apart fluid tension relief slots 378 are circumferentially arranged in membrane frame top 358 about midway between its perimeter and that of circular aperture 374. Ventilator 210 may also be exposed to water or other liquids. Tension relief slots 378 also provide escape paths for residual amounts of water or other liquid that, because of surface tension, could become trapped in membrane assembly 350 and consequently cause deviation from expected gas pressure values during operation. The components of membrane assembly 350, which include membrane frame top 358, membrane film 352, and membrane frame bottom 360, are held together by circumferentially spaced-apart circular nibs 380 extending through holes 382 in membrane film 352 and holes 384 in membrane frame bottom 360. Spatially associated holes 382 and 384 are in axial alignment. Holes 382 and holes 384 are circumferentially arranged near the perimeter of, respectively, membrane film 352 and membrane frame bottom 360 and allow outflow of glue or heat seal material that secures together the components of membrane assembly 350.

With particular reference to FIGS. 10A, 10B, 11, 13A, 13B, 15A, 15B, 15C, 15D, and 15E, a spring tension selector lid 390 has formed on its interior surface 391 a central aperture 392 and an internal single-turn spiral race 394. Spiral race 394 has a center 396 and is sized to receive spring adjustment support cam 324 when spring tension selector lid 390 is snap fit over lid connector central locating pin 348 and held in place onto pressure adjustment portion 218. Rotating spring tension selector lid 390 in one direction causes support cam 324 to travel along and away from center 396 of spiral race 394 and thereby move along rectangular guide slot 298 toward the perimeter of pressure adjustment portion 218. Moving support cam 324 away from center 396 of spiral race 394 stretches extension spring 344 and thereby applies increasing force by membrane frame-contacting surface 328 against top surface 376 of boss 370. Rotating spring tension selector lid 390 in the opposite direction causes support cam 324 to travel along and toward center 396 of spiral race 394 and thereby move along rectangular guide slot 298 away from the perimeter of pressure adjustment portion 218. Moving support cam 324 toward center 396 of spiral race 394 relaxes extension spring 344 and thereby applies decreasing force by membrane frame-contacting surface 328 against top surface 376 of boss 370. Spring tension selector lid 390 has formed on its exterior surface 398 a raised dial grip 400 in the shape of an arrow to enable manual rotation of spring tension selector lid 390. A U-clip flexor 402 formed on interior surface 391 and positioned at the perimeter of spring tension selector lid 390 fits between indexing slots 404 of a gas pressure indicating cap 406 to hold fast spring tension selector lid 390 to a gas pressure value selected by a user.

Gas pressure indicating cap 406 is configured for placement over spring tension selector lid 390 and pressure adjustment portion 218 and has a central opening 408 of sufficient size to provide user access to dial grip 400. Gas pressure indicating cap 406 is embossed with numerical values 410 mutually spaced part around central opening 408 to represent different displacements of extension spring 344 and thus force applied to membrane film 352 by boss 370 against membrane force adapter 356 in response to a user rotating spring tension selector lid 390. While numerical values 410 are depicted as embossed or raised upon gas pressure indicating cap 406 in the embodiment shown here, in an alternative embodiment, numerical values 410 could be recessed into the surface of gas pressure indicating cap 406 or otherwise flattened to facilitate manufacturability of the part. Numerical values 410 are calibrated to pressure values (PIP values) that correspond directly to the tension in extension spring 344 and the position of spring adjustment support cam 324 along rectangular slot 298. Gas pressure indicating cap 406 has three downwardly depending locking lugs 412 that are suitably spaced apart to fit into gaps 228*g* and thereby prevent rotational unlocking and detachment of pressure adjustment portion 218 from base portion 216 and inadvertent rotation or lifting of spring tension selector lid 390. Gas pressure indicating cap 406 also has two downwardly depending flexure clips 414 terminating in locking tabs 416 to provide a snap fit into spatially aligned notches 418 (only one shown in FIG. 11) formed in side wall 284 of pressure adjustment portion 218.

Manual backup tab 330 may be used to manually control or override the force applied by membrane frame-contacting surface 328 of lever arm 326 against top surface 376 of boss 370. Depressing manual backup tab 330 towards valve body 212 causes rotation of lever arm 326 about pivot pins 342 to raise membrane frame-contacting surface 328 away from top surface 376 of boss 370, thereby diminishing or eliminating the downward force applied to top surface 376 of boss 370. Lifting manual backup tab 330 away from valve body 212 causes rotation of lever arm 326 about pivot pins 342 to increase the force applied by membrane frame-contacting surface 328 to top surface 376 of boss 370. Thus, manual backup tab 330 may be employed by a user to manually hold ventilator 210 in an open or closed configuration, thereby enabling manual control of gas pressure cycling by overriding the gas pressure cycling that occurs in normal operation.

Figure 10A:
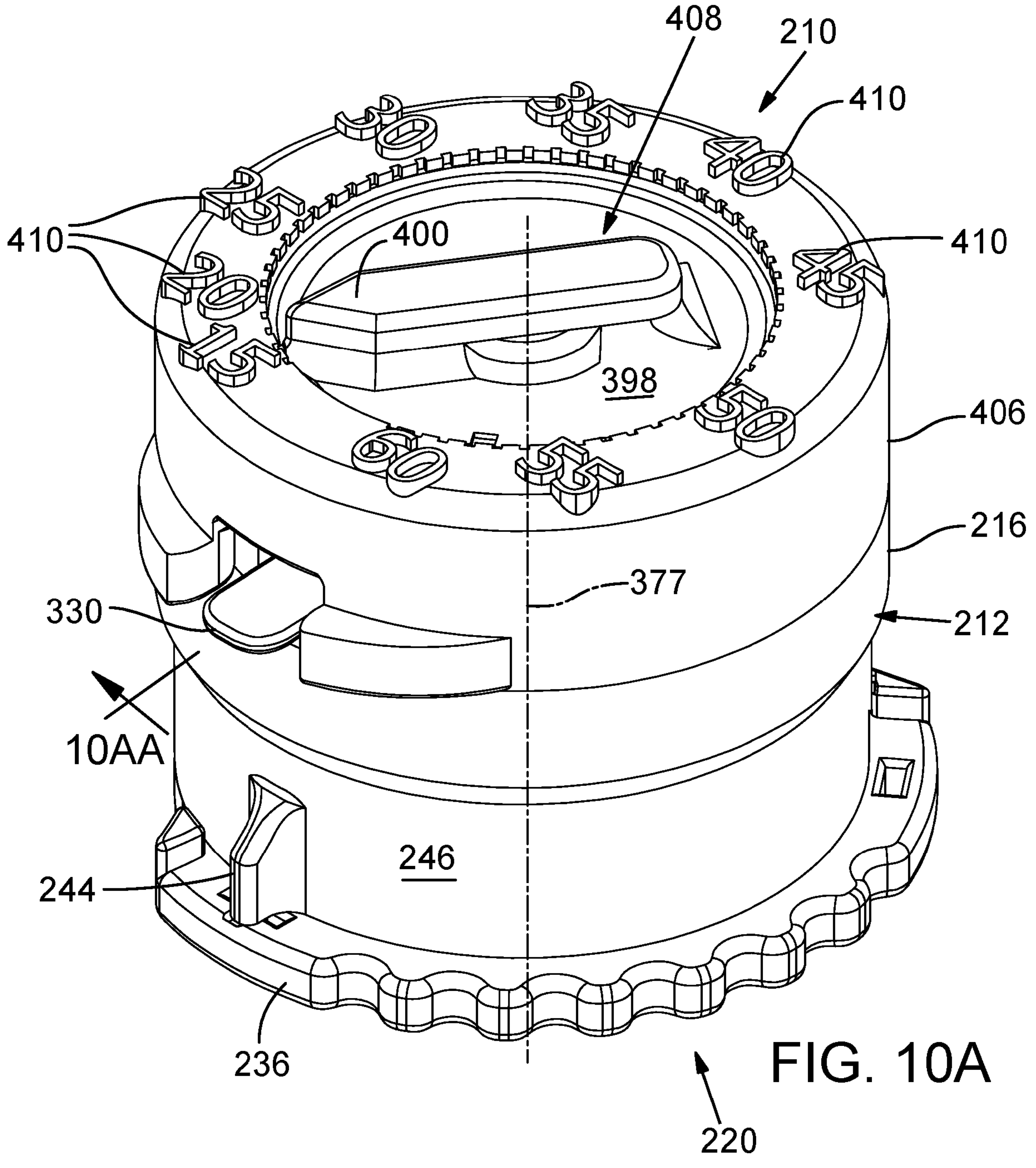
FIGS. 10A, 10B, 10C, and 10D are, respectively, isometric, top plan, right-side, and rear-side exterior views of a second embodiment of the disclosed gas-driven, pressure-regulated ventilator.
Figures 10B, 10C:
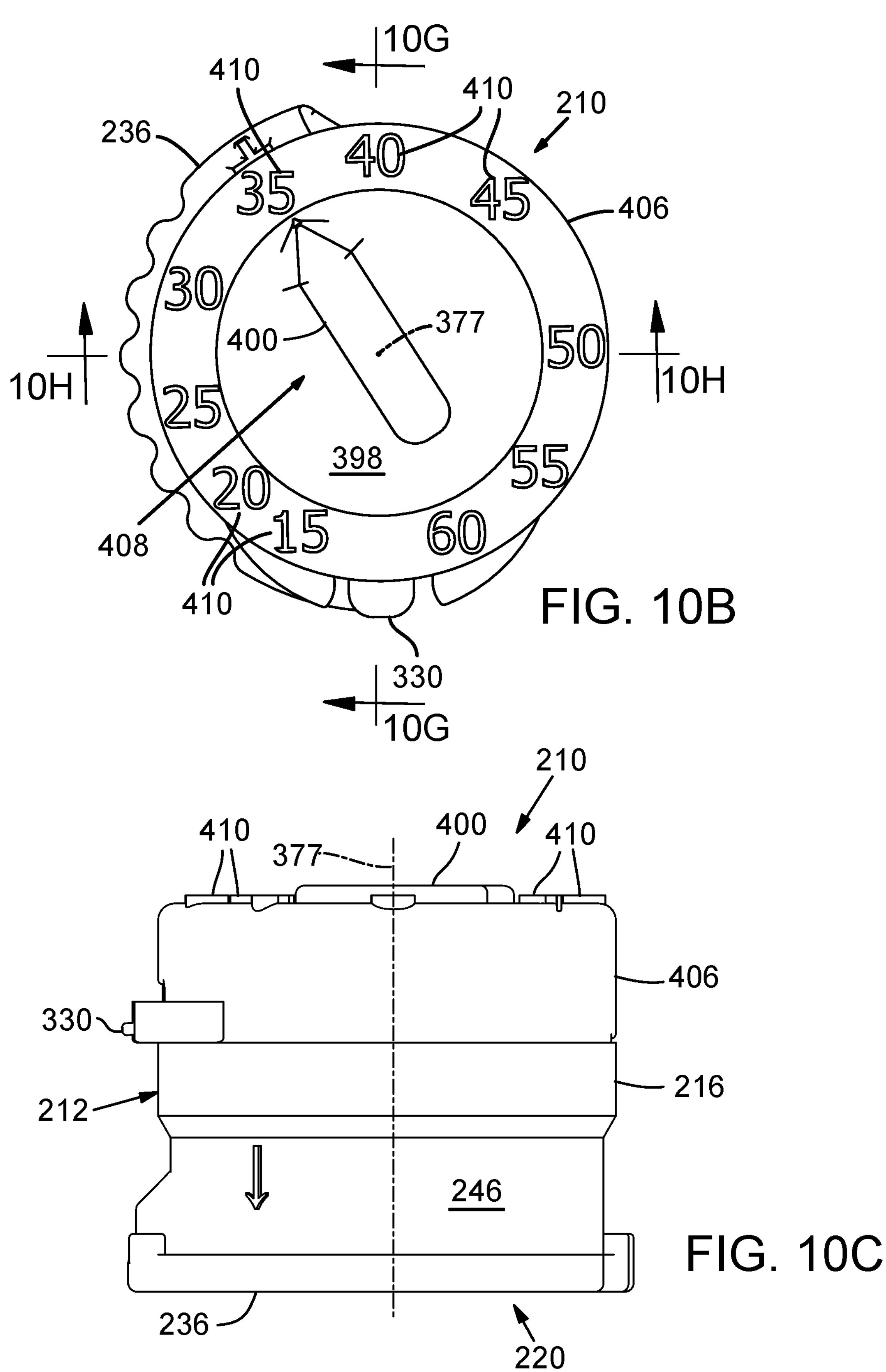

The length and pitch of spiral race 394 is set in coordination with the spring constant of extension spring 344 to govern the amount of force imparted to boss 370 by membrane frame-contacting surface 328 of lever arm 326 as spring tension selector lid 390 is rotated. Accordingly, the shape of spiral race 394 may be configured to impart a nonlinear force profile as spring attachment support cam 324 is translated along rectangular guide slot 298 within spiral race 394 as spring tension selector lid 390 is rotated. This may be useful, for example, to calibrate spring tension selector lid 390 such that certain ranges of rotational position have higher resolution for finer adjustment of spring tension (and corresponding PIP values) than other rotational positions. FIGS. 10A and 10B show, for example, nonuniformly spaced dial gauge pressure indicators 410 having nonuniformly spaced pressure values of 15, 20, 25, 35, 40, 45, 50, 55, and 60 of cm$H_2O$ with increased spacing between 40 to 60 cm$H_2O$. Such a calibration is advantageous, for example, to increase the sensitivity of PIP adjustment at pressure levels between 40 to 60 cm $H_2O$ where the lungs of some patients may be susceptible to barotrauma injury if PIP levels applied during mechanical ventilation therapy are too high.

Figures 10D, 10E:
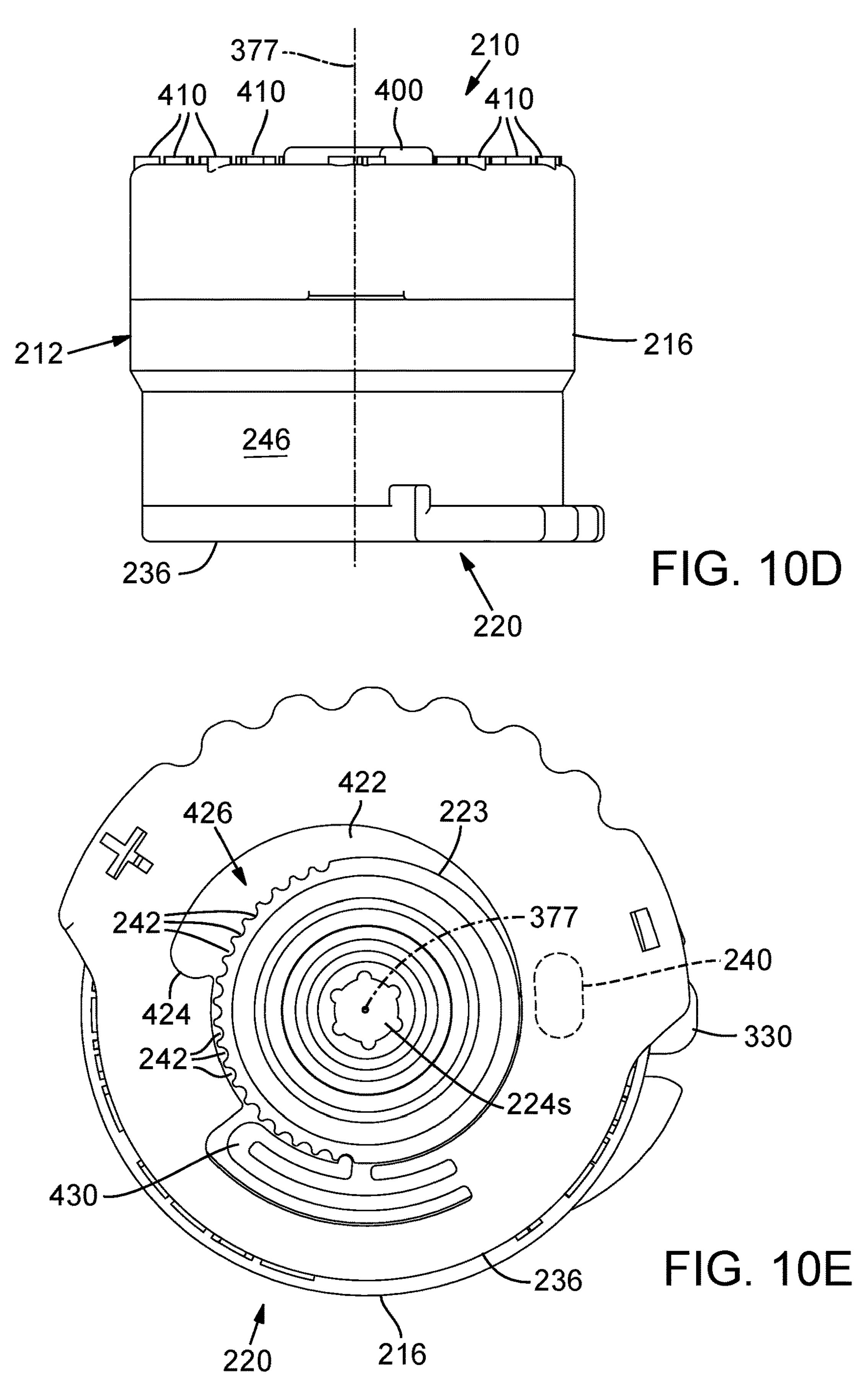
FIGS. 10E and 10F are bottom plan exterior views of the ventilator of FIGS. 10A-10D shown with its gas flow rate selector dial in different rotational positions.
Figure 10F:
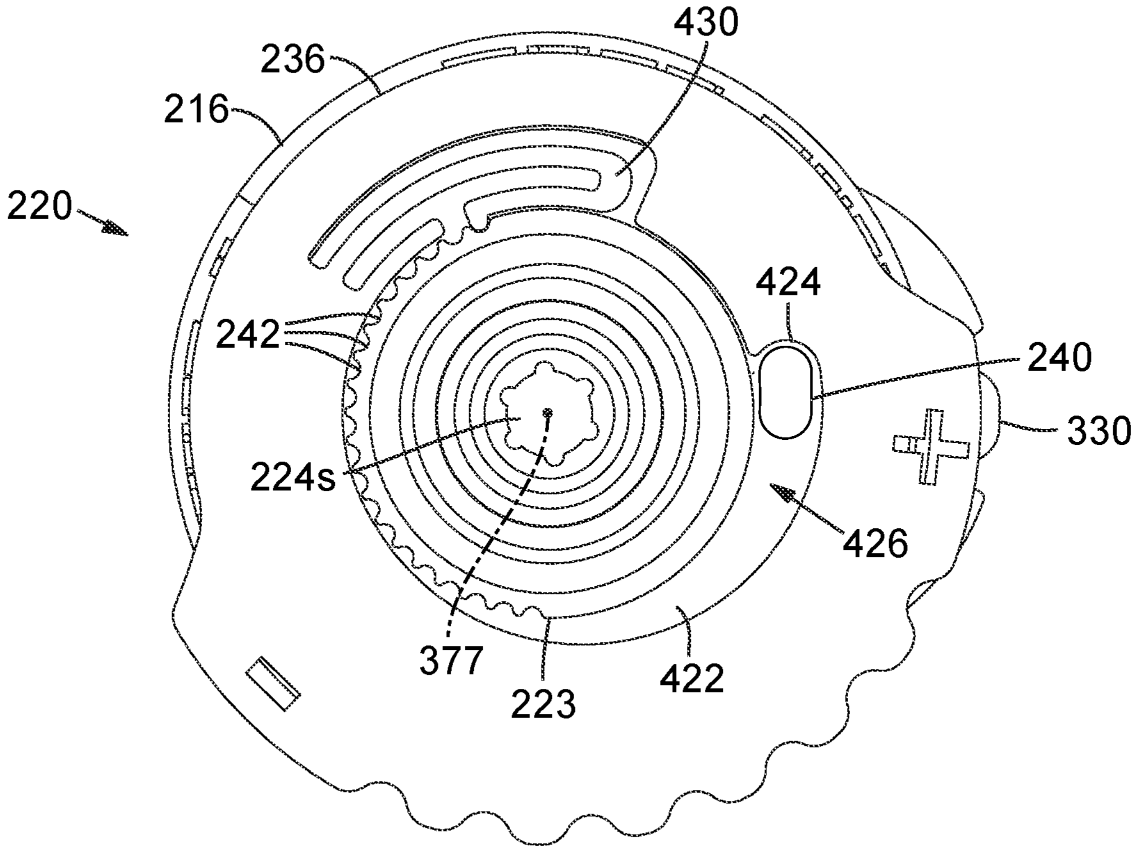
Figures 16A, 16B:
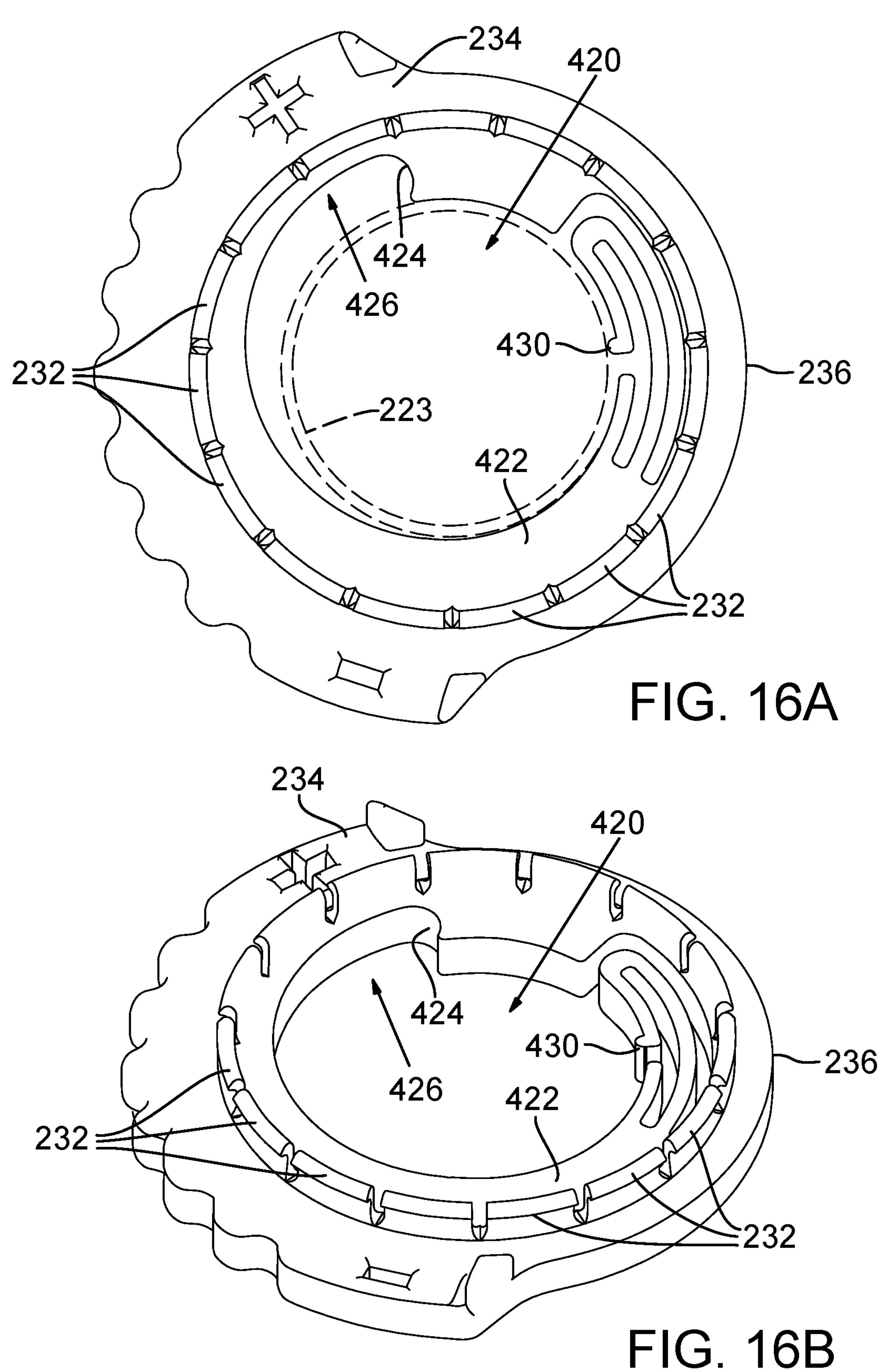
FIGS. 16A and 16B are, respectively, top plan and oblique views of the interior of a gas flow rate selector dial of the ventilator of FIGS. 10A-10F.

With particular reference to FIGS. 10E, 10F, 12B, 16A, and 16B, gas flow rate selector dial 236 includes a central open space 420 bounded by an inner circumferential portion 422 of decreasing area that terminates in an arcuate section 424. When assembled with base portion 216, inner circumferential portion 422 forms in cooperation with outwardly extending section 223 a tapered arcuate slot 426 that is set radially so that its widest open portion is spatially aligned with gas outlet through-hole 240. FIG. 16A shows inner circumferential portion 223 in phantom lines to illustrate formation of tapered arcuate slot 426. A user rotating rate selector dial 236 aligns gas outlet through-hole 240 with continuously varying amounts of open space of tapered arcuate slot 426 to control the amount of gas flow exhausted from base portion 216. FIG. 10E shows ventilator 210 with gas flow rate selector dial 236 rotated to a position in which tapered arcuate slot 426 is not aligned with gas outlet through-hole 240. FIG. 10F shows ventilator 210 with gas flow rate selector dial 236 rotated clockwise so that tapered arcuate slot 426 is substantially aligned with gas outlet through-hole 240 to permit gas exhaust from base portion 216.

A U-clip flexor 430 is formed on inner circumferential portion 422 and positioned inside of tabs 232 of rate selector dial 236. U-clip flexor 430 is radially aligned with and sized to fit in indexing slots 242 in outwardly extending circular section 223 for purpose of producing a clicking sound as a user rotates rate selector dial 236 to adjust the rate of gas flow from base portion 216.

Figure 10G:
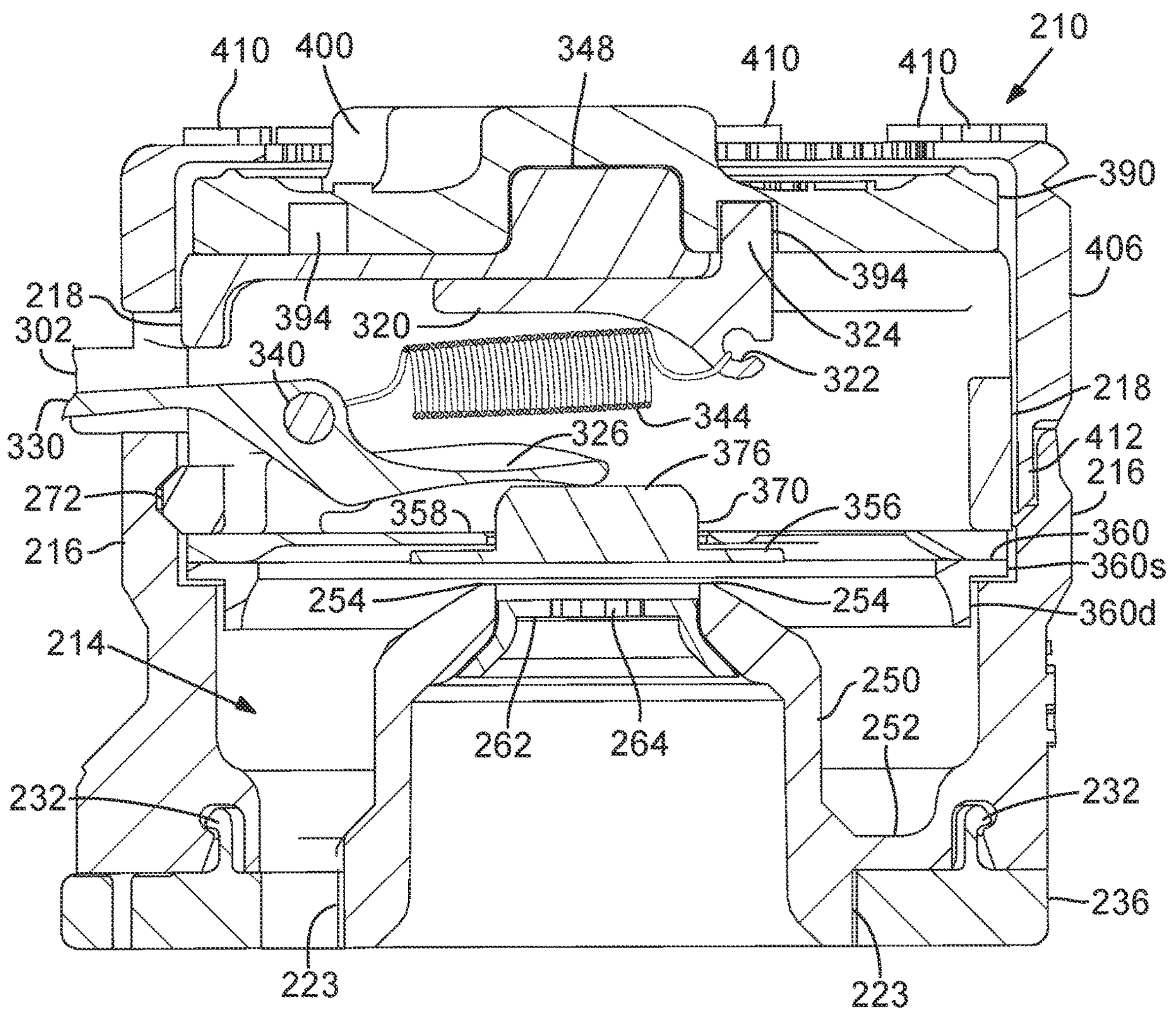
FIGS. 10G and 10H are sectional views taken along, respectively, lines 10G-10G and lines 10H-10H of FIG. 10B.
Figure 10H:
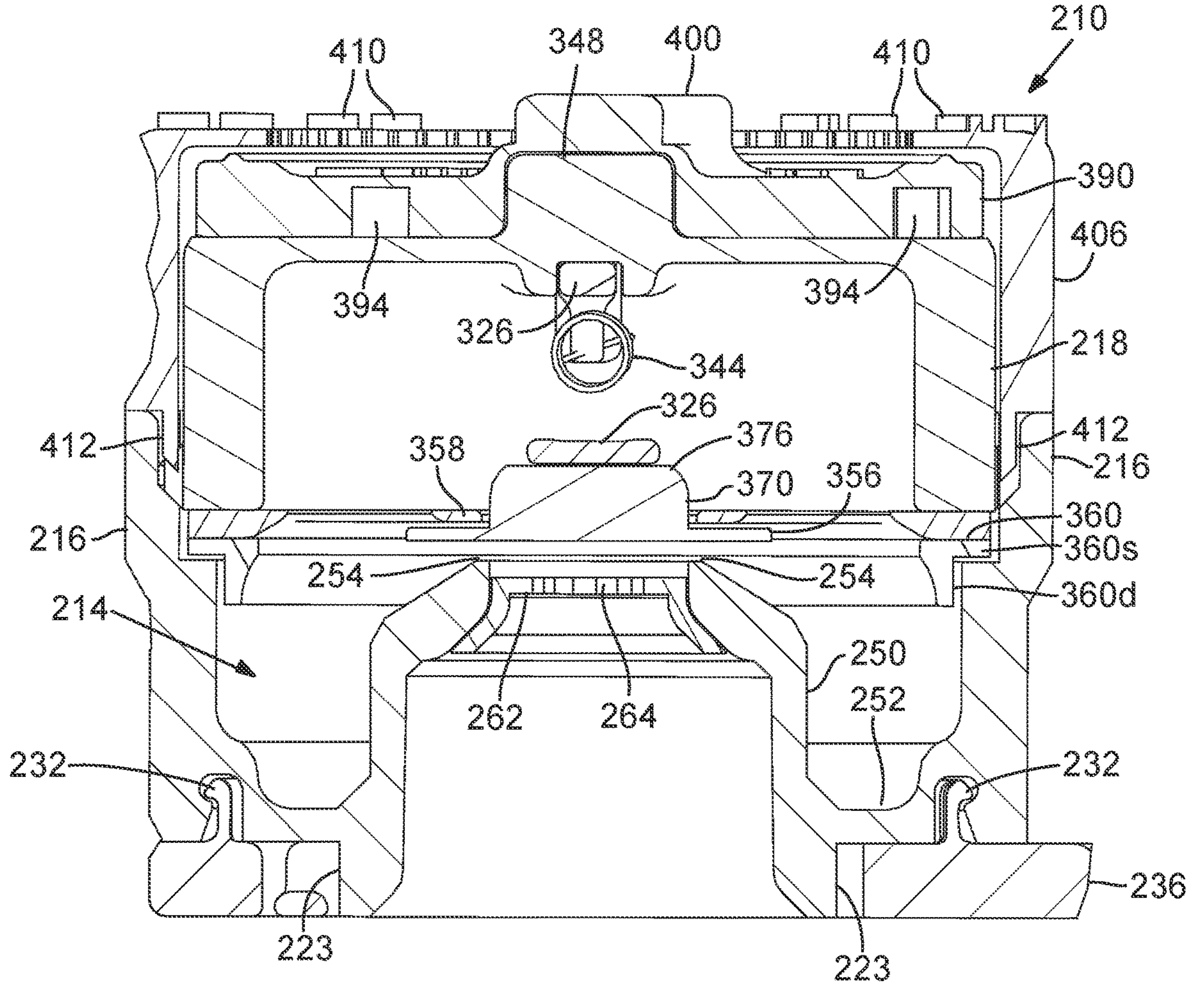

Ventilator 210 operates in a gas-driven, pressure-regulated manner to cycle between open and closed states in the same manner as that described for the embodiment of ventilator 10 and depicted in FIGS. 8A and 8B. Application of the embodiment of ventilator 210 to FIGS. 8A and 8B entails inserting first tee-branch 122 of tee-adapter 120 into central gas inlet opening 224. In the embodiment of ventilator 10, actuation between open and closed states is performed by piston 70 translating longitudinally within valve body 12; and, in the embodiment of ventilator 210, actuation between open and closed states is performed by membrane assembly 350. When ventilator 210 is assembled as depicted in FIGS. 10A, 10G, and 10H, membrane assembly 350 is disposed within valve body 212 such that the bottom surface of shoulder portion 360*s* of membrane frame bottom 360 is clamped against internal mounting rim 362 by the downward force exerted on membrane frame top 358 by pressure adjustment portion 218. In this assembled configuration, membrane assembly 350 is fixed securely in place along its perimeter. Membrane force adapter 356, housed within membrane assembly 350 and bounded on its membrane-contacting surface 366 by membrane film 352 and its opposite surface 368 by membrane frame top 358, is configured for movement along longitudinal axis 377 of valve body 212 by a travel distance of about 0.5 mm to about 2.0 mm with boss 370 extending through circular aperture 374 of membrane frame top 358. In this configuration, membrane force adapter 356 and membrane film 352 serve as an actuator to cyclically alternate between closed and open configurations to obstruct or permit gas flow, respectively, from breathing gas pathway 124 into valve body 212.

In the closed position, membrane contacting surface 366 of membrane force adapter 356 is in contact with membrane film 352 and held in place against sealing rim 254 by the downward force exerted on boss 370 by membrane frame-contacting surface 328 of lever arm 326, thereby forming an airtight seal to obstruct the flow of gas into interior 214 of valve body 212. During operation, when ventilator 210 is in this closed position, pressure buildup in breathing gas pathway 124 produces a steadily increasing net upward force acting over an area $A_{closed}$ of gas-receiving surface 364 of membrane film 352 circumscribed by sealing rim 254 at central opening 260. When this net upward force matches and exceeds the downward force provided by lever arm 326, the airtight seal about sealing rim 254 is interrupted, allowing pressure within gas pathway 124 to act over a full surface area $A_{open}$ of gas-receiving surface 364 of membrane film 352, increasing the net upward force and causing a transition of ventilator 210 to the open configuration. In this open configuration, gas flow is permitted into interior 214 of valve body 212 where it is exhausted through gas outlet through-hole 240. This re-direction of gas flow through valve body 212 and out gas outlet through-hole 240 results in exhalation of air from patient's lungs 136 and concomitant reduction in pressure in the breathing gas pathway 124.

Figure 17:
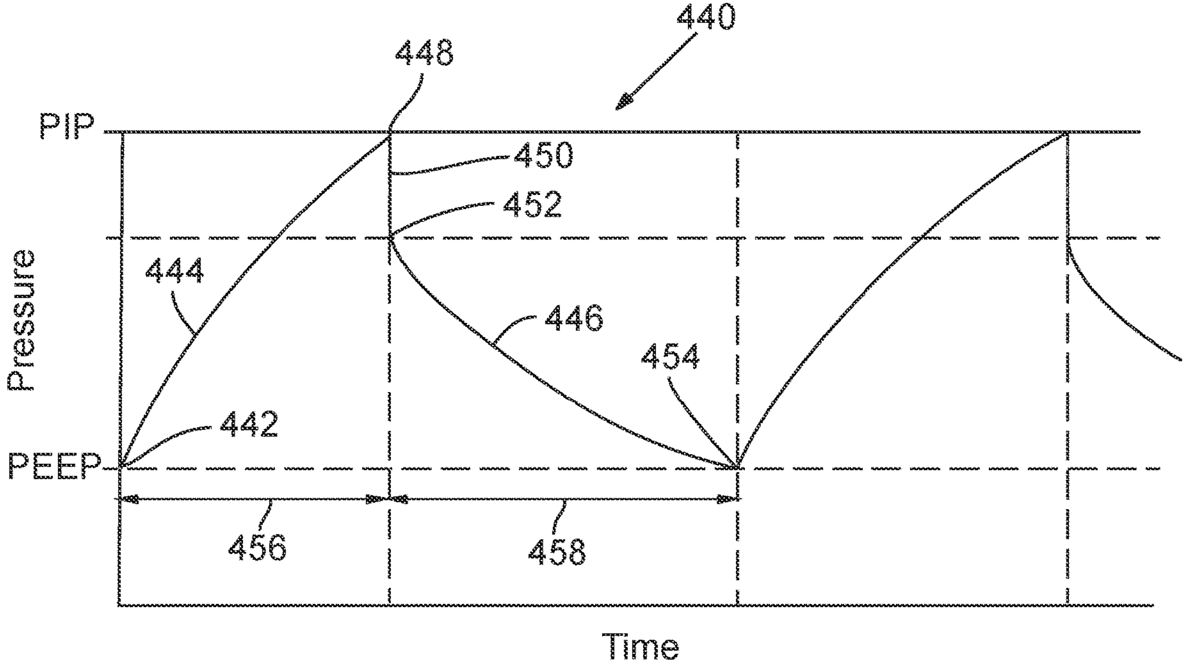
FIG. 17 is an exemplary plot of gas pressure versus time during a breath cycle, including inhalation followed by exhalation, under control of an embodiment of the disclosed ventilator.

FIG. 17 shows an exemplary plot of gas pressure versus time during a breath cycle 440 beginning at a minimum pressure value 442 and comprising a pressure rise during inhalation 444 followed by pressure fall during exhalation 446 under control of ventilator 210. The presence of orifice plate 262 within tubular member 250 below sealing rim 254 in ventilator 210, in combination with the actuation of membrane assembly 360, alters the shape of the pressure versus time plot compared to that shown in FIG. 9 and corresponding to ventilator 10. In particular, immediately after the maximum pressure value 448 at inhalation is reached with ventilator 210 (i.e., when pressure reaches the PIP value), a step-wise pressure drop 450 from PIP to a lower pressure value 452 occurs, after which the pressure falls in an exponential manner over time to approach a PEEP value 454. Lower pressure value 452 following stepwise pressure drop 450 corresponds to the plateau pressure, a clinically relevant indicator of the pressure the alveoli and small airways of the lung are exposed to during mechanical ventilation. In addition, inclusion of orifice plate 262 within the breathing circuit increases the stability with which membrane assembly 350 repetitively cycles between the open and closed configuration during operation. Accordingly, the ratio of inhalation duration 456 to exhalation duration 458 over breath cycle 440—referred to as the I:E ratio in clinical nomenclature—is stabilized. Together, the manifestation of the stepwise pressure drop 450 to the lower pressure value 452 and the stabilization of the I:E ratio observed during operation of ventilator 210 allows it to more closely match the pressure profiles seen in conventional electromechanical ventilator devices.

The embodiment of ventilator 210 as described herein may be used to mechanically ventilate subjects in a pressure-controlled mode by placing the device in-line in a breathing circuit between a pressurized gas source and a patient's airway and lungs in the same manner as that depicted in FIGS. 8A and 8B. The operator can use ventilator 210 to deliver adjustable ventilation suitable for both neonatal and adult subjects ranging in weight from 2.5 kg to over 250 kg. Ventilator 210 may also be used in situations in which patients have significant airway obstruction, for example, up to 75 cm $H_2O$/Us for adults and 200 cm $H_2O$/L/s for infants. The adjustable range of PIP values is 0-50 cm $H_2O$ when an auxiliary pressure relief valve is incorporated into the breathing circuit, and 0-60 cm$H_2O$ without this additional safety feature. PEEP value is related to the set PIP value and varies according to a ratio in the range of about 1:3 to 1:5 dependent on the fixed ratio between surface areas exposed to gas pressure in the closed and open configurations (i.e., $A_{closed}/A_{open}$), the rate of inflow of gas from a pressurized gas source, and individual patient parameters including patient weight, airway resistance, and lung compliance. Exhalation duration can be adjusted by rotating gas flow rate selector dial 236, which is tuned to enable inhalation: exhalation time ratios (that is, I:E ratios) from 1:1 to 1:4, as desired by an operator. Ventilator 210 is also designed for easy assembly and disassembly without the use of tools, so that an operator can quickly clean or clear the device of any solid or liquid obstructions such as vomitus, or break down and reassemble the device for cleaning or sterilization.

As with ventilator 10, ventilator 210 is configured to allow a clinician or operator to adjust the magnitude of PIP and PEEP values, and adjust the duration of inhalation and exhalation flows in a breath cycle to accommodate patient-specific ventilation needs. An exemplary procedure by which an operator might adjust ventilator 210 to accommodate a patient's needs is as follows. First, the operator would set a prescribed rate of inflow of gas from a pressurized gas source based on patient weight, airway resistance, and lung compliance. Next, the operator would rotate spring tension selector lid 390 to select a prescribed PIP value. This PIP value, in combination with the rate of inflow of gas from pressurized gas source, would establish a corresponding PEEP value. Next, the operator would set a desired duration of exhalation by rotating gas flow rate selector dial 236 to adjust the rate of outflow of gas from valve body 212 when ventilator 210 is in the open configuration. Operator would then perform a check with a manometer to confirm that the PIP and PEEP values are in the desired range. If needed, the operator would adjust gas flow rate selector dial 236 and rate of inflow of gas from a pressurized gas source to fine tune the pressure profile and inhalation and exhalation durations administered to the patient.

It will be obvious to those having skill in the art that many changes may be made to the details of the above-described embodiments without departing from the underlying principles of the invention. The scope of the present invention should, therefore, be determined only by the following claims.

The invention claimed is:

1. A gas-driven, pressure-regulated ventilator, comprising:

a hollow valve body including an interior and a breathing gas pathway in fluid communication with a gas inlet for supply of gas flow within the interior of the valve body, the valve body having first and second ends and defining a longitudinal axis, and the valve body including pressure adjustment open space and a gas inlet opening and a gas outlet opening, the pressure adjustment open space located nearer to the first end, and the gas inlet and gas outlet openings located nearer to the second end;

an adjustable peak inspiratory pressure (PIP) valve mechanism operatively associated with the valve body and including:

a gas-pressure responsive displacement member having a contact surface that, in response to pressure applied by flow of gas along the breathing gas pathway, changes position within the interior of the valve body between open and closed positions along the longitudinal axis, and the gas-pressure responsive displacement member assuming the closed position in absence of gas flow within the interior of the valve body;

a spring support member operatively connected to the valve body and to a spring-actuated member that extends into the pressure adjustment open space and applies a force against the contact surface of the gas-pressure responsive displacement member, the force applied in a direction opposite to that of force applied to the gas-pressure responsive displacement member by the flow of gas along the breathing gas pathway; and a spring adjustment device operatively connected to the spring-actuated member for adjusting the force applied against the contact surface of the gas-pressure responsive displacement member; and an adjustable gas flow rate valve mechanism operatively associated with the valve body and including a gas flow rate adjustment device configured to allow, in cooperation with the gas outlet opening, a controllable amount of gas flow out of the valve body when the gas-pressure responsive displacement member is in the open position, and in which the valve body is of generally cylindrical shape and comprises a base portion and a detachable pressure adjustment portion, the base portion including, at a first end, a first locking feature, and, at a second end, a base floor, the base floor including the gas inlet opening from which a tubular member extends into the interior of the valve body and terminates in a sealing rim at a free end, and the pressure adjustment portion including a second locking feature configured to mate with the first locking feature to releasably secure together the base portion and the pressure adjustment portion.

2. The ventilator of claim 1, in which the adjustable gas flow rate valve mechanism includes a flow control dial that in cooperation with an arcuate slot allows an increasing amount of gas flow through the gas outlet opening in response to rotation of the flow control dial to cause more complete alignment of the arcuate slot with the gas outlet opening.

3. The ventilator of claim 1, in which the pressure adjustment portion includes a pressure adjustment portion floor, the interior of the valve body includes a mounting rim that is positioned nearer to the base floor than is the sealing rim of the tubular member, and the gas-pressure responsive displacement member comprises a membrane assembly that has a circumferential side surface and is configured for placement on the mounting rim of the base portion, the membrane assembly including a membrane film contacting a membrane force adapter and positioned between a first membrane frame and a second membrane frame, the membrane force adapter having a membrane-contacting surface and an opposite surface from which a boss extends, the first membrane frame configured as a disk having a central aperture sized to receive the boss of the membrane force adapter, and the second membrane frame configured as a ring having interior space through which the membrane film can flex in directions along the longitudinal axis.

4. The ventilator of claim 3, in which the membrane film has a perimeter near which through holes are arranged in spaced apart relation, and in which the first membrane frame, the membrane film, and the second membrane frame are held together by nibs coupled to first and second membrane frames and extending through the holes in the membrane film.

5. The ventilator of claim 3, in which the membrane film is a silicone sheet characterized by a durometer Shore A hardness scale of between about 40 and about 60.

6. The ventilator of claim 3, in which the first membrane frame includes multiple fluid tension relief slots spaced apart around the central aperture.

7. The ventilator of claim 1, in which the gas outlet opening is formed in the base floor of the base portion of the valve body.

8. The ventilator of claim 1, in which the sealing rim at the free end of the tubular member defines a first opening having a first area, and further comprising an orifice plate set within the tubular member at a distance below the sealing rim and defining a second opening having a second area that is less than the first area.

9. The ventilator of claim 8, in which the first and second openings are circular and the second opening has a periphery around and into which mutually spaced-apart notches are formed.

10. The ventilator of claim 8, in which the orifice plate is formed as an integral part of the tubular member.

11. The ventilator of claim 1, in which the pressure adjustment portion includes a pressure adjustment portion floor, the pressure adjustment open space of the pressure adjustment portion has an inner side wall, and a spring operatively connects the spring support member and the spring-actuated member, the spring support member comprising a spring tension slider that is movable along a guide slot formed in the pressure adjustment portion floor, and the spring-actuated member comprising a lever arm that is pivotally mounted to pivot pin catches formed at an open portion of the inner side wall of the pressure adjustment portion.

12. The ventilator of claim 11, in which the pressure adjustment portion has a side wall in which is formed a side wall opening, and in which an end of the lever arm extends outward through the side wall opening to provide manual control of gas pressure cycling.

13. The ventilator of claim 11, in which the spring is of an extension spring type.

14. The ventilator of claim 11, in which the pressure adjustment portion has a top wall from which a central locating pin outwardly projects, and in which the spring tension slider has an end from which a spring attachment support cam extends through the guide slot and is configured for support on and bidirectional travel along the top wall.

15. The ventilator of claim 14, further comprising a spring tension selector lid having an interior surface in which are formed a central aperture and an internal spiral race, the central aperture sized to receive the central locating pin extending from the pressure adjustment portion and the spiral race sized to receive the spring attachment support cam, the spiral race having a pitch configured so that rotation of the spring tension selector lid causes the support cam to travel along the spiral race and thereby move along guide slot to change the extension of the spring.

16. The ventilator of claim 15, in which the spring tension selector lid has an exterior surface on which a dial grip is formed to enable manual rotation of the spring tension selector lid.

17. The ventilator of claim 16, further comprising a gas pressure indicating cap configured for placement over the spring tension selector lid, the cap having an opening providing user access to the dial grip, and the cap having around its periphery symbols indicating dial settings calibrated to peak inspiratory pressure (PIP) values that correspond to extension of the spring and position of the support cam along the guide slot.

18. The ventilator of claim 17, in which the gas pressure indicating cap includes locking tabs configured for insertion into the base portion to prevent rotation of the cap and the pressure adjustment portion when a user manually rotates the dial grip to set a PIP value.

19. The ventilator of claim 1, in which the valve body has a side surface into which the gas outlet opening is formed.

20. The ventilator of claim 1, in which the gas-pressure responsive displacement member includes a piston in the form of a cup having a circumferential side surface and a bottom, the bottom bounded by interior and exterior surfaces and including a raised elastomeric seal affixed to the interior surface and a boss extending away from the exterior surface to form the contact surface, the raised elastomeric seal affixed to the interior surface of the bottom of the piston configured to mount on the sealing rim at the free end of the tubular member, and a tubular member extends from the pressure adjustment open space of the pressure adjustment portion and is sized to receive the boss of the piston when the gas-pressure responsive displacement member is in the open position.

21. A gas-driven, pressure-regulated ventilator, comprising:

a hollow valve body including an interior and a breathing gas pathway in fluid communication with a gas inlet for supply of gas flow within the interior of the valve body, the valve body having first and second ends and defining a longitudinal axis, and the valve body including pressure adjustment open space and a gas inlet opening and a gas outlet opening, the pressure adjustment open space located nearer to the first end, and the gas inlet and gas outlet openings located nearer to the second end;

an adjustable peak inspiratory pressure (PIP) valve mechanism operatively associated with the valve body and including:

a gas-pressure responsive displacement member having a contact surface that, in response to pressure applied by flow of gas along the breathing gas pathway, changes position within the interior of the valve body between open and closed positions along the longitudinal axis, and the gas-pressure responsive displacement member assuming the closed position in absence of gas flow within the interior of the valve body;

a spring support member operatively connected to the valve body and to a spring-actuated member that extends into the pressure adjustment open space and applies a force against the contact surface of the gas-pressure responsive displacement member, the force applied in a direction opposite to that of force applied to the gas-pressure responsive displacement member by the flow of gas along the breathing gas pathway; and a spring adjustment device operatively connected to the spring-actuated member for adjusting the force applied against the contact surface of the gas-pressure responsive displacement member; and an adjustable gas flow rate valve mechanism operatively associated with the valve body and including a gas flow rate adjustment device configured to allow, in cooperation with the gas outlet opening, a controllable amount of gas flow out of the valve body when the gas-pressure responsive displacement member is in the open position, in which the spring-actuated member has a distal end and a spring connection tab, the distal end of the spring-actuated member applying the contact force against the gas-pressure responsive displacement member, and in which the spring support member is tubular and has a threaded outer surface configured for threaded engagement with a spring tension adjustment nut, and the tubular spring support member further comprises two diametrically opposed lengthwise slots, the tubular spring support member containing a spring having first and second ends, the first end of the spring operatively connected to a spring hanger support bar extending through the two slots in the tubular spring support member and resting against the spring tension adjustment nut, and the second end of the spring operatively connected to the spring connection tab of the spring-actuated member.

22. The ventilator of claim 21, in which the spring is of an extension spring type.

23. The ventilator of claim 22, in which the tubular member of the pressure adjustment portion has a partly open side wall, and further comprising a pivot pin passing through the partly open side wall of the tubular member, the pivot pin supporting the spring-actuated member for pivotal movement in applying the force against the contact surface of the piston.

24. The ventilator of claim 21, in which the adjustable gas flow rate valve mechanism includes a flow control dial that in cooperation with an arcuate slot allows an increasing amount of gas flow through the gas outlet opening in response to rotation of the flow control dial to cause more complete alignment of the arcuate slot with the gas outlet opening.

* * * * *